US007687052B2

United States Patent
Kung et al.

(10) Patent No.: US 7,687,052 B2
(45) Date of Patent: *Mar. 30, 2010

(54) STYRYLPYRIDINE DERIVATIVES AND THEIR USE FOR BINDING AND IMAGING AMYLOID PLAQUES

(75) Inventors: Hank F. Kung, Winnewood, PA (US); Mei-Ping Kung, Winnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/727,401

(22) Filed: Mar. 26, 2007

(65) Prior Publication Data

US 2008/0038195 A1 Feb. 14, 2008

Related U.S. Application Data

(60) Provisional application No. 60/787,156, filed on Mar. 30, 2006.

(51) Int. Cl.
*A61K 51/00* (2006.01)
*C07D 213/62* (2006.01)
(52) U.S. Cl. ..................... 424/1.89; 546/300
(58) Field of Classification Search ........... 546/300; 564/442; 424/1.89

See application file for complete search history.

(56) References Cited

U.S. PATENT DOCUMENTS

| 5,506,089 | A | 4/1996 | Gybin et al. | |
|---|---|---|---|---|
| 7,297,820 | B2 * | 11/2007 | Kung et al. | 564/336 |
| 2006/0269473 | A1 * | 11/2006 | Kung et al. | 424/1.11 |
| 2006/0269474 | A1 * | 11/2006 | Kung et al. | 424/1.11 |
| 2008/0253967 | A1 | 10/2008 | Kung et al. | |

FOREIGN PATENT DOCUMENTS

WO 99/02497 A2 1/1999

OTHER PUBLICATIONS

Ono, M. et al., "Synthesis and biological evaluation of (E)-3-styrylpyridine derivatives as amyloid imaging agents for Alzheimer's disease," Nuclear Medicine and Biology, 2005, 32, 329-335.
Jerchel, D. et al., "Kondensation von Methylpyridinen mit Benzaldehyd," Justus Liebigs Annalen Der Chemie, Verlag Chemie GMBH, Weinheim, DE, vol. 613, 1958, pp. 171-177.
Honma, Y. et al., "Antiallergic Agents. 3. N-(1H-tetrazol-5-yl)-2-pyridinecarboxamides," Journal of Medicinal Chemistry, American Chemical Society, Washington, US, vol. 27, No. 2, 1984, pp. 125-128.

(Continued)

*Primary Examiner*—Janet L Andres
*Assistant Examiner*—Binta M Robinson
(74) *Attorney, Agent, or Firm*—Woodcock Washburn LLP

(57) ABSTRACT

This invention relates to a method of imaging amyloid deposits and to styrylpyridine compounds, and methods of making radiolabeled styrylpyridine compounds useful in imaging amyloid deposits. This invention also relates to compounds, and methods of making compounds for inhibiting the aggregation of amyloid proteins to form amyloid deposits, and a method of delivering a therapeutic agent to amyloid deposits.

11 Claims, 9 Drawing Sheets

OTHER PUBLICATIONS

Database CA (online) Chemical Abstracts Service, Kupetis, G. K. et al., "Synthesis of some quaternary styrylpyridinium salts," retrieved from STN Database Accession No. 1998:36725 & Chemija, (3), 98-101, 1997.

Database CA (online) Chemical Abstracts Service, Wyrzykiewicz, E. et al., "New N-substituted derivatives of E-2'- and E-3' - hyroxystilbazoles-(4) of potential antimicrobial activity," retrieved from STN Database Accession No. 1991:160578 & Pharmazie, 45(10), 790-1, 1990.

Database CA (online) Chemical Abstracts Service, Lapucha, A. R., "Heterocyclic analogs of stilbenes: reactions of (E)-4-azastilbenes with polymethylene dibromides," retrieved from STN Database Accession No. 1989:23689 & Polish Journal of Chemistry, 61(4-6), 563-7, 1987.

Park, S. H. et al., "Studies of charge resonance bands formed in .alpha.- and .gamma. -styrylpyridinium tetraphenylborate derivatives," Journal of Photopolymer Science and Technology, 14(2), 227-232, 2001, p. 228.

Ginsberg, S. D. et al., "Molecular Pathology of Alzheimer's Disease and Related Disorders," in Cerebral Cortex: Neurodegenerative and Age-related Changes in Structure and Function of Cerebral Cortex, Kluwer Academic/Plenum, NY (1999), pp. 603-654.

Vogelsberg-Ragaglia, V. et al., "Cell Biology of Tau and Cytoskeletal Pathology in Alzheimer's Disease," Alzheimer's Disease, Lippincot, Williams & Wilins, Philadelphia, PA (1999), pp. 359-372.

Xia, W. et al., "Presenilin complexes with the C-terminal fragments of amyloid precursor protein at the sites of amyloid beta-protein generation," Proc. Natl. Acad. Sci. USA, 2000, 97, 9299-9304.

Selkoe, D., "The origins of Alzheimer disease: a is for amyloid," JAMA, 2000, 283, 1615-1617.

Wolfe, M. S. et al., "A substrate-based difluoro ketone selectively inhibits Alzheimer's gamma-secretase activity," J. Med. Chem., 1998, 41, 6-9.

Skovronsky, D. M. et al., "Beta-secretase revealed: starting gate for race to novel therapies for Alzheimer's disease," Trends Pharmacol. Sci., 2000, 21, 161-163.

Selkoe, D. J., "Biology of β-amyloid Precursor Protein and the Mechanism of Alzheimer's Disease," Alzheimer's Disease, Lippincott Williams & Wilkins, Philadelphia, PA (1999), pp. 293-310.

Naslund, J. et al., "Correlation Between Elevated Levels of Amyloid β-Peptide in the Brain and Cognitive Decline," J. Am. Med. Assoc., 2000, 283, 1571-1577.

Golde, T. E. et al., "Biochemical detection of Abeta isoforms: implications for pathogenesis, diagnosis, and treatment of Alzheimer's disease," Biochimica et Biophysica Acta, 2000, 1502, 172-187.

Vassar, R. et al., "Beta-secretase cleavage of Alzheimer's amyloid precursor protein by the transmembrane aspartic protease BACE," Science, 1999, 286, 735-741.

Kung, M.-P. et al., "Characterization of IMPY as a potential imaging agent for b-amyloid plaques in double transgenic PSAPP mice," Eur. J. Nucl. Med. Mol. Imaging, 2004, 31, 1136-1145.

Moore, C. L. et al., "Difluoro ketone peptidomimetics suggest a large S1 pocket for Alzheimer's gamma-secretase: implications for inhibitor design," J. Med. Chem., 2000, 43, 3434-3442.

Findeis, M. A., "Approaches to discovery and characterization of inhibitors of amyloid beta-peptide polymerization," Biochimica et Biophysica Acta, 2000, 1502, 76-84.

Kuner, P. et al., "Controlling polymerization of beta-amyloid and prion-derived peptides with synthetic small molecule ligands," J. Biol. Chem., 2000, 275, 1673-1678.

Elhaddaoui, a. et al., "Competition of Congo Red and Thioflavin S Binding to Amyloid Sites in Alzheimer's Diseased Tissue," Biospectroscopy, 1995, 1, 351-356.

Shoghi-Jadid, K. et al., "Localization of neurofibrillary tangles and beta-amyloid plaques in the brains of living patients with Alzheimer disease," Am. J. Geriatr. Psychiatry, 2002, 10, 24-35.

Nordberg, A., "PET imaging of amyloid in Alzheimer's disease," Lancet Neurol., 2004, 3, 519-527.

Agdeppa, E. D. et al., "In vitro detection of (S)-naproxen and ibuprofen binding to plaques in the Alzheimer's brain using the positron emission tomography molecular imaging probe 2-(1-[6-[(2-[(18)F]fluoroethyl)(methyl)amino]-2-naphthyl]ethylidene)malononitrile," Neuroscience, 2003, 117, 723-730.

Mathis, C. A. et al., "Imaging beta-amyloid plaques and neurofibrillary tangles in the aging human brain," Curr. Pharm. Des., 2004, 10, 1469-1492.

Mathis, C. A. et al., "Imaging technology for neurodegenerative diseases: progress toward detection of specific pathologies," Arch. Neurol., 2005, 62, 196-200.

Kung, M-P. et al., "Binding of two potential imaging agents targeting amyloid plaques in postmortem brain tissues of patients with Alzheimer's disease," Brain Res., 2004, 1025(1-2), 98-105.

Verhoeff, N. P. et al., "In-vivo imaging of Alzheimer disease beta-amyloid with [11C]SB-13 PET," Am. J. Geriatr. Psychiatry, 2004, 12, 584-595.

Berge, S. M. et al., "Pharmaceutical Salts," J. Pharm. Sci., 1977, 66, 1-19.

Patani et. al., "Bioisosterism: A Rational Approach in Drug Design", Chem. Rev. 1996, 96, 3147-3176.

\* cited by examiner

| $K_i$ = 6.7 nM; PC = 2.41 | $K_i$ = 6.7 nM; PC = 3.22 |

AD Brain Homogenates/IMPY

| Compound | $K_i$ (nM ± SEM) |
|---|---|
| 2 | 2.5 ± 0.4 |
| 5 | 150 ± 30 |
| 6 | 10 ± 3.3 |
| 8 | 91.2 ± 8.7 |
| 9 | 2.2 ± 0.2 |
| 11a | 6.8 ± 1.4 |
| 11b | 4.5 ± 0.9 |
| 11e | 14.2 ± 0.9 |
| 13a | 7.5 ± 0.8 |
| 13b | 9.0 ± 1.0 |
| 13e | 21 ± 8.0 |
| 14a | 3.6 ± 0.8 |
| 14b | 5.0 ± 1.6 |
| 14e | 6.8 ± 0.8 |
| 16a | 7.5 ± 1.5 |
| 16b | 8.5 ± 2.5 |
| 16e | 15.5 ± 0.5 |

Potencies ($K_i$) of compounds for displacement of I-125-IMPY binding to amyloid plaques in AD brain homogenates

FIG. 5

STYRYLPYRIDINE DERIVATIVES AND THEIR USE FOR BINDING AND IMAGING AMYLOID PLAQUES

CROSS REFERENCE TO RELATED APPLICATIONS

This application claims the benefit of Provisional Application No. 60/787,156, filed Mar. 30, 2006, the contents of which are entirely incorporated by reference herein.

STATEMENT REGARDING FEDERALLY-SPONSORED RESEARCH AND DEVELOPMENT

Part of the work performed during development of this invention utilized U.S. Government funds. The U.S. Government has certain rights in this invention under grant numbers AG-022559 and AG-021868 awarded by the National Institutes of Health.

BACKGROUND OF THE INVENTION

1. Field of the Invention

This invention relates to novel styrylpyridine compounds, the uses thereof in diagnostic imaging and inhibiting amyloid-β aggregation, and methods of making these compounds.

2. Background Art

Alzheimer's disease (AD) is a progressive neurodegenerative disorder characterized by cognitive decline, irreversible memory loss, disorientation, and language impairment. Postmortem examination of AD brain sections reveals abundant senile plaques (SPs) composed of amyloid-β (Aβ) peptides and numerous neurofibrillary tangles (NFTs) formed by filaments of highly phosphorylated tau proteins (for recent reviews and additional citations see Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins. Formation and accumulation of aggregates of β-amyloid (Aβ) peptides in the brain are critical factors in the development and progression of AD.

In addition to the role of amyloid deposits in Alzheimer's disease, the presence of amyloid deposits has been shown in diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

The fibrillar aggregates of amyloid peptides, $A\beta_{1-40}$ and $A\beta_{1-42}$, are major metabolic peptides derived from amyloid precursor protein found in senile plaques and cerebrovascular amyloid deposits in AD patients (Xia, W., et al., *J. Proc. Natl. Acad. Sci. U.S.A.* 97:9299-9304 (2000)). Prevention and reversal of Aβ plaque formation are being targeted as a treatment for this disease (Selkoe, D., J. JAMA 283:1615-1617 (2000); Wolfe, M. S., et al., J. Med. Chem. 41:6-9 (1998); Skovronsky, D. M., and Lee, V. M., *Trends Pharmacol. Sci.* 21:161-163 (2000)).

Familial AD (FAD) is caused by multiple mutations in the A precursor protein (APP), presenilin 1 (PS1) and presenilin 2 (PS2) genes (Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

While the exact mechanisms underlying AD are not fully understood, all pathogenic FAD mutations studied thus far increase production of the more amyloidogenic 42-43 amino-acid long form of the Aβ peptide. Thus, at least in FAD, dysregulation of Aβ production appears to be sufficient to induce a cascade of events leading to neurodegeneration. Indeed, the amyloid cascade hypothesis suggests that formation of extracellular fibrillar Aβ aggregates in the brain may be a pivotal event in AD pathogenesis (Selkoe, D. J., "Biology of β-amyloid Precursor Protein and the Mechanism of Alzheimer's Disease," *Alzheimer's Disease*, Lippincot Williams & Wilkins, Philadelphia, Pa. (1999), pp. 293-310; Selkoe, D. J., *J. Am. Med. Assoc.* 283:1615-1617 (2000); Naslund, J., et al., *J. Am. Med. Assoc.* 283:1571-1577 (2000); Golde, T. E., et al., *Biochimica et Biophysica Acta* 1502:172-187 (2000)).

Various approaches in trying to inhibit the production and reduce the accumulation of fibrillar Aβ in the brain are currently being evaluated as potential therapies for AD (Skovronsky, D. M. and Lee, V. M., *Trends Pharmacol. Sci.* 21:161-163 (2000); Vassar, R., et al., *Science* 286:735-741 (1999); Wolfe, M. S., et al., *J. Med. Chem.* 41:6-9 (1998); Moore, C. L., et al., *J. Med. Chem.* 43:3434-3442 (2000); Findeis, M. A., *Biochimica et Biophysica Acta* 1502:76-84 (2000); Kuner, P., Bohrmann, et al., *J. Biol. Chem.* 275:1673-1678 (2000)). It is therefore of interest to develop ligands that specifically bind fibrillar Aβ aggregates. Since extracellular SPs are accessible targets, these new ligands could be used as in vivo diagnostic tools and as probes to visualize the progressive deposition of Aβ in studies of AD amyloidogenesis in living patients.

To this end, several interesting approaches for developing fibrillar Aβ aggregate-specific ligands have been reported (Ashburn, T. T., et al., *Chem. Biol.* 3:351-358 (1996); Han, G., et al., *J. Am. Chem. Soc.* 118:4506-4507 (1996); Klunk, W. E., et al., *Biol. Psychiatry* 35:627 (1994); Klunk, W. E., et al., *Neurobiol. Aging* 16:541-548 (1995); Klunk, W. E., et al., *Society for Neuroscience Abstract* 23:1638 (1997); Mathis, C. A., et al., *Proc. XIIth Intl. Symp. Radiopharm. Chem., Uppsala, Sweden:*94-95 (1997); Lorenzo, A. and Yankner, B. A., *Proc. Natl. Acad. Sci. U.S.A.* 91:12243-12247 (1994); Zhen, W., et al., *J. Med. Chem.* 42:2805-2815 (1999)). The most attractive approach is based on highly conjugated chrysamine-G (CG) and Congo red (CR), and the latter has been used for fluorescent staining of SPs and NFTs in post-mortem AD brain sections (Ashburn, T. T., et al., *Chem. Biol.* 3:351-358 (1996); Klunk, W. E., et al., *J. Histochem. Cytochem.* 37:1273-1281 (1989)). The inhibition constants ($K_i$) for binding to fibrillar Aβ aggregates of CR, CG, and 3'-bromo- and 3'-iodo derivatives of CG are 2,800, 370, 300 and 250 nM, respectively (Mathis, C. A., et al., *Proc. XIIth Intl. Symp. Radiopharm. Chem., Uppsala, Sweden:*94-95 (1997)). These compounds have been shown to bind selectively to Aβ (1-40) peptide aggregates in vitro as well as to fibrillar Aβ deposits in AD brain sections (Mathis, C. A., et al., *Proc. XIIth Intl. Symp. Radiopharm. Chem., Uppsala, Sweden:*94-95 (1997)).

There are several potential benefits of imaging Aβ aggregates in the brain. The imaging technique will improve diagnosis by identifying potential patients with excess Aβ plaques in the brain; therefore, they may be likely to develop Alzheimer's disease. It will also be useful to monitor the progression of the disease. When anti-plaque drug treatments become available, imaging Aβ plaques in the brain may provide an essential tool for monitoring treatment. Thus, a simple, noninvasive method for detecting and quantitating amyloid deposits in a patient has been eagerly sought. Presently, detection of amyloid deposits involves histological analysis of biopsy or autopsy materials. Both methods have drawbacks. For example, an autopsy can only be used for a postmortem diagnosis.

The direct imaging of amyloid deposits in vivo is difficult, as the deposits have many of the same physical properties (e.g., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules have provided some selectivity on the periphery of tissues, but have provided for poor imaging of tissue interiors.

Potential ligands for detecting Aβ aggregates in the living brain must cross the intact blood-brain barrier. Thus brain uptake can be improved by using ligands with relatively smaller molecular size (compared to Congo Red) and increased lipophilicity. Highly conjugated thioflavins (S and T) are commonly used as dyes for staining the Aβ aggregates in the AD brain (Elhaddaoui, A., et al., *Biospectroscopy* 1:351-356 (1995)).

A highly lipophilic tracer, [$^{18}$F]FDDNP, for binding both tangles (mainly composed of hyperphosphorylated tau protein) and plaques (containing Aβ protein aggregates) has been reported. (Shoghi-Jadid K, et al., *Am J Geriatr Psychiatry.* 2002; 10:24-35). Using positron-emission tomography (PET), it was reported that this tracer specifically labeled deposits of plaques and tangles in nine AD patients and seven comparison subjects. (Nordberg A. *Lancet Neurol.* 2004; 3:519-27). Using a novel pharmacokinetic analysis procedure called the relative residence time of the brain region of interest versus the pons, differences between AD patients and comparison subjects were demonstrated. The relative residence time was significantly higher in AD patients. This is further complicated by an intriguing finding that FDDNP competes with some NSAIDs for binding to Aβ fibrils in vitro and to Aβ plaques ex vivo (Agdeppa E D, et al. 2001; Agdeppa E D, et al., *Neuroscience.* 2003; 117:723-30).

Imaging β-amyloid in the brain of AD patients by using a benzothiazole aniline derivative, [$^{11}$C]6-OH-BTA-1 (also referred to as [$^{11}$C]PIB), was recently reported. (Mathis C A, et al., *Curr Pharm Des.* 2004; 10:1469-92; Mathis C A, et al., *Arch. Neurol.* 2005, 62:196-200.). Contrary to that observed for [$^{18}$F]FDDNP, [$^{11}$C]6-OH-BTA-1 binds specifically to fibrillar Aβ in vivo. Patients with diagnosed mild AD showed marked retention of [$^{11}$C]6-OH-BTA-1 in the cortex, known to contain large amounts of amyloid deposits in AD. In the AD patient group, [$^{11}$C]6-OH-BTA-1 retention was increased most prominently in the frontal cortex. Large increases also were observed in parietal, temporal, and occipital cortices and in the striatum. [$^{11}$C]6-OH-BTA-1 retention was equivalent in AD patients and comparison subjects in areas known to be relatively unaffected by amyloid deposition (such as subcortical white matter, pons, and cerebellum). Recently, another $^{11}$C labeled Aβ plaque-targeting probe, a stilbene derivative-[$^{11}$C]SB-13, has been studied. In vitro binding using the [$^{3}$H]SB-13 suggests that the compound showed excellent binding affinity and binding can be clearly measured in the cortical gray matter, but not in the white matter of AD cases. (Kung M-P, et al., *Brain Res.* 2004; 1025:89-105. There was a very low specific binding in cortical tissue homogenates of control brains. The Kd values of [$^{3}$H]SB-13 in AD cortical homogenates were 2.4±0.2 nM. High binding capacity and comparable values were observed (14-45 pmol/mg protein) (Id.). As expected, in AD patients [$^{11}$C]SB-13 displayed a high accumulation in the frontal cortex (presumably an area containing a high density of Aβ plaques) in mild to moderate AD patients, but not in age-matched control subjects. (Verhoeff N P, et al., *Am J Geriatr Psychiatry.* 2004; 12:584-95).

It would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

SUMMARY OF THE INVENTION

The present invention provides novel compounds of Formulae I, Ia, II and III.

The present invention also provides diagnostic compositions comprising a radiolabeled compound of Formulae I, Ia, II and III a pharmaceutically acceptable carrier or diluent.

The invention further provides a method of imaging amyloid deposits, the method comprising introducing into a patient a detectable quantity of a labeled compound of Formulae I, Ia, II and III or a pharmaceutically acceptable salt, ester, amide or prodrug thereof.

The present invention also provides a method for inhibiting the aggregation of amyloid proteins, the method comprising administering to a mammal an amyloid inhibiting amount of a compound Formulae I, Ia, II and III or a pharmaceutically acceptable salt, ester, amide, or prodrug thereof.

A further aspect of this invention is directed to methods and intermediates useful for synthesizing the amyloid inhibiting and imaging compounds of Formulae I, Ia, II and III described herein.

DESCRIPTION OF THE FIGURES

FIG. 5 depicts several compounds of the present invention and their respective binding data.

DETAILED DESCRIPTION OF THE INVENTION

Figure 1:
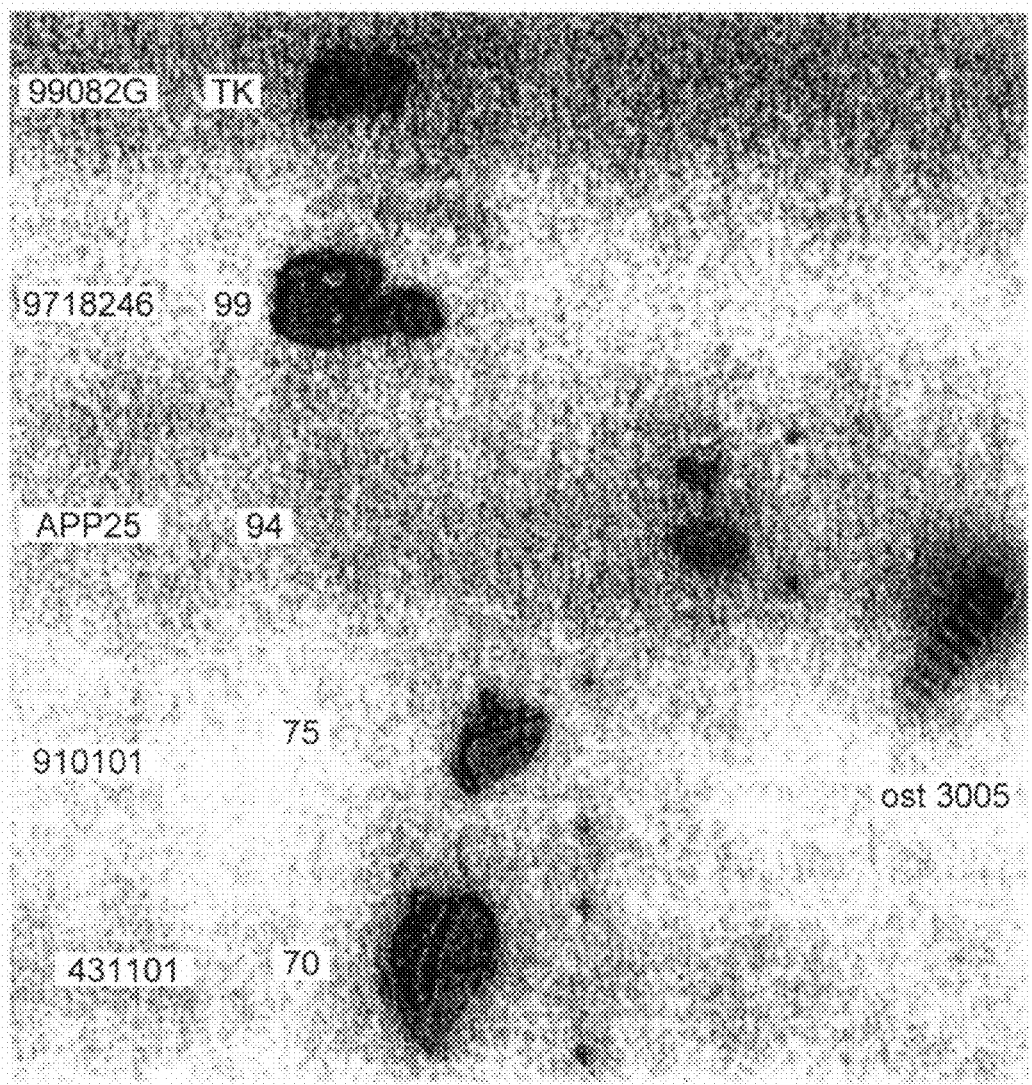
FIG. 1 depicts a film resulting from the imaging of a compound of the present invention.

A compound of Formula I,

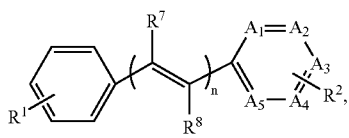

I or a pharmaceutically acceptable salt thereof; wherein, n is an integer from one to six; at least one, no more than three, of $A_1$, $A_2$, $A_3$, $A_4$ and $A_5$ is N, the others are —CH or —CR$^2$ as permitted; R$^1$ is selected from the group consisting of:
   a. —(CH$_2$)$_p$NR$^a$R$^b$, wherein R$^a$ and R$^b$ are independently hydrogen, C$_{1-4}$ alkyl, hydroxy(C$_{1-4}$)alkyl or halo(C$_{1-4}$)alkyl, and p is an integer from 0 to 5;
   b. hydroxy,
   c. C$_{1-4}$ alkoxy,
   d. hydroxy(C$_{1-4}$)alkyl,
   e. halogen,
   f. cyano,
   g. hydrogen,
   h. nitro,
   i. (C$_1$-C$_4$)alkyl,
   j. halo(C$_1$-C$_4$)alkyl,
   k. formyl,
   l. —NHCO(C$_{1-4}$ alkyl), and
   m. —OCO(C$_{1-4}$ alkyl);

R$^2$ is selected from the group consisting of:

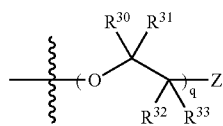

i wherein q is an integer from 1 to 10; Z is selected from the group consisting of halogen, halogen substituted benzoyloxy, halogen substituted benzyloxy, halogen substituted phenyl (C$_{1-4}$)alkyl, halogen substituted aryloxy, and a halogen substituted C$_{6-10}$ aryl, or Z can also be hydroxy; and R$^{30}$, R$^{31}$, R$^{32}$ and R$^{33}$ are in each instance independently selected from the group consisting of hydrogen, hydroxy, C$_{1-4}$ alkoxy, C$_{1-4}$ alkyl, and hydroxy(C$_{1-4}$)alkyl; or Z is hydroxy;

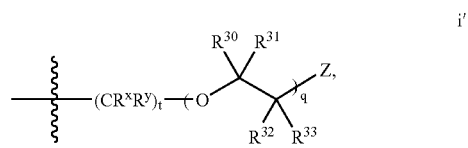

i' wherein q is an integer from 1 to 10, R$^x$ and R$^y$ are hydrogen, hydroxy or C$_{1-4}$ alkyl; t is 0, 1, 2 or 3; and Z, R$^{30}$, R$^{31}$, R$^{32}$ and R$^{33}$ are as described above;

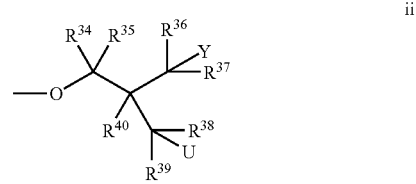

ii wherein Y is selected from the group consisting of halogen, halogen substituted benzoyloxy, halogen substituted phenyl (C$_{1-4}$)alkyl, halogen substituted aryloxy, and halogen substituted C$_{6-10}$ aryl; U is selected from the group consisting of hydrogen, hydroxy, halogen, halogen substituted benzoyloxy, halogen substituted phenyl(C$_{1-4}$)alkyl, halogen substituted aryloxy, and halogen substituted C$_{6-10}$ aryl; and R$^{34}$, R$^{35}$, R$^{36}$, R$^{37}$, R$^{38}$, R$^{39}$ and R$^{40}$ are in each instance independently selected from the group consisting of hydrogen, halogen, hydroxy, C$_{1-4}$ alkoxy, C$_{1-4}$ alkyl, and hydroxy(C$_{1-4}$)alkyl;

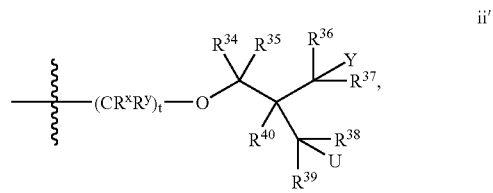

ii' wherein R$^x$ and R$^y$ are hydrogen, hydroxy or C$_{1-4}$ alkyl; t is 0, 1, 2 or 3; and Y, U, R$^{34}$, R$^{35}$, R$^{36}$, R$^{37}$, R$^{38}$, R$^{39}$ and R$^{40}$ are as described above;
   iii. NR'R", wherein at least one of R' and R" is (CH$_2$)$_d$X, where X is halogen, preferably F or $^{18}$F, and d is an integer from 1 to 4; the other of R' and R" is selected from the group consisting of hydrogen, C$_{1-4}$ alkyl, halo (C$_{1-4}$)alkyl, and hydroxy(C$_{1-4}$)alkyl;
   iv. NR'R"—(C$_{1-4}$)alkyl, wherein at least one of R' and R" is (CH$_2$)$_d$X, where X is halogen, preferably F or $^{18}$F, and d is an integer from 1 to 4; the other of R' and R" is selected from the group consisting of hydrogen, C$_{1-4}$ alkyl, halo (C$_{1-4}$)alkyl, and hydroxy(C$_{1-4}$)alkyl;
   v. halo(C$_{1-4}$)alkyl; and
   vi. an ether (R—O—R) having the following structure: [halo(C$_{1-4}$)alkyl-O—(C$_{1-4}$)alkyl]-; and R$^7$ and R$^8$ are in each instance independently selected from the group consisting of hydrogen, hydroxy, amino, methylamino, dimethylamino, C$_{1-4}$ alkoxy, C$_{1-4}$ alkyl, and hydroxy (C$_{1-4}$)alkyl.

Preferred compounds include those where the halogen, in one or more occurrence on the structure, is a radiolabeled halogen. Also preferred are compounds wherein the halogen is selected from the group consisting of I, $^{123}$I, $^{125}$I, $^{131}$I, Br, $^{76}$Br, $^{77}$Br, F or $^{18}$F. Especially preferred compounds are those that contain $^{18}$F. Compounds containing $^{123}$I are also especially preferred.

Useful values of $R^1$ are listed above. Preferred values are hydroxy or $NR^aR^b(CH_2)_p$—, wherein p is an integer from 0 to 5, and $R^a$ and $R^b$ are independently hydrogen, $C_{1-4}$ alkyl or $(CH_2)_dX$, where X is halogen, and d is an integer from 1 to 4 Useful values of p include integers from 0 to 5. Preferably, p is 0, 1 or 2. Most preferably, p is 0 such that $R^1$ represents $NR^aR^b$. In preferred embodiments, $R^1$ is either in the meta or para position relative to the respective bridge. A preferred value of $R^1$ is $NR^aR^b$, wherein $R^a$ and $R^b$ are independently hydrogen or $C_{1-4}$ alkyl. In this embodiment, it is preferable that the $C_{1-4}$ alkyl is methyl. Preferably one of $R^a$ and $R^b$ is hydrogen, the other is $C_{1-4}$ alkyl, such as methyl. Most preferably, both $R^a$ and $R^b$ are methyl. Another preferred value of $R^1$ is hydroxy. Also preferred are any prodrug groups that after administration yield a preferred value of $R^1$. Such prodrug groups are well-known in the art.

Useful values of n include integers from 1 to 6. Preferably, the value of n is from 1 to 4. Most preferably, the value of n is from 1 to 3. It is especially preferred that n is one.

Useful values of $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl. The value of n determines the number of $R^7$ and $R^8$ group(s) present in the compound. If present more than once in a particular compound, in each instance of $R^7$ and $R^8$ the value can be different from any other value of $R^7$ and $R^8$. In preferred embodiments, $R^7$ and $R^8$ are each hydrogen in every instance.

Useful values of $R^2$ include substructures i, i', ii, ii', iii, iv, v, and vi, as depicted above. In preferred embodiments of Formula I, $R^2$ is either in the meta or para position relative to the respective bridge. Preferably, $R^2$ is substructure i or ii. Also preferred are substructures i' and ii'. In these embodiments, useful values of q include integers from one to ten. Preferably, in a compound where $R^2$ is i or i', q is an integer from 1 to 5. Most preferably, q is 1 to 4, especially 3 or 4. In substructure i or i', useful values of $R^{30}$, $R^{31}$, $R^{32}$ and $R^{33}$ independently include hydrogen, hydroxy, $C_{1-4}$ alkoxy, $C_{1-4}$ alkyl, and hydroxy($C_{1-4}$)alkyl. Preferred compounds include those where one or more of $R^{30}$, $R^{31}$, $R^{32}$ and $R^{33}$ are hydrogen. More preferred compounds include those where each of $R^{30}$, $R^{31}$, $R^{32}$ and $R^{33}$ is hydrogen.

In substructure ii or ii', useful values of Y, U and $R^{34}$, $R^{35}$, $R^{36}$, $R^{37}$, $R^{38}$, $R^{39}$ and $R^{40}$ are described above. Preferred compounds include those where U is hydroxy.

Useful compounds include those compounds where at least one, no more than three, of $A_1$, $A_2$, $A_3$, $A_4$ and $A_5$ is N, and the others are —CH or —$CR^2$ as permitted. It is more preferred that N be in position $A_4$.

Preferred compounds of Formula I include those compounds wherein $A_4$ is N, having the following formula:

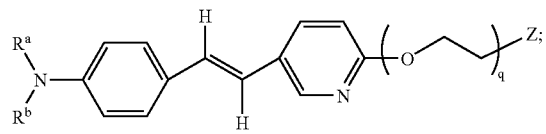

wherein $R^a$ and $R^b$ are independently selected from hydrogen or $C_1$-$C_4$ alkyl, Z is as described above and q is an integer from 1 to 5. Examples of preferred compounds include:

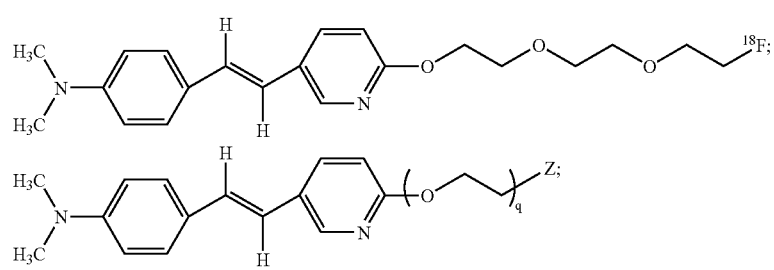

wherein q is integer from 1 to 4; such as,

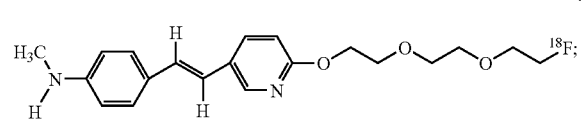

Other preferred compounds of Formula I, when $R^2$ is ii, include:

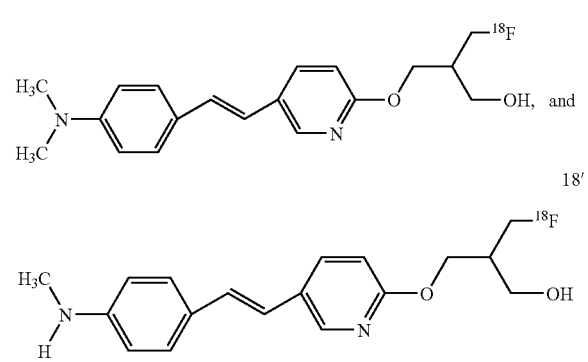

In another aspect, the present invention is directed to compounds of Formula I, having the following structure:

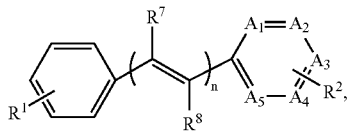

or a pharmaceutically acceptable salt thereof, wherein: at least one, no more than three, of $A_1$, $A_2$, $A_3$, $A_4$ and $A_5$ is N, the others are —CH, or —$CR^2$ as permitted; n is an integer from 1 to 6; $R^1$ includes all useful values described above, preferably hydroxy or $NR^aR^b(CH_2)_p$—, wherein p is an integer from 0 to 5, and $R^a$ and $R^b$ are independently hydrogen, $C_{1-4}$ alkyl or $(CH_2)_dX$, where X is halogen, and d is an integer from 1 to 6; $R^2$ is selected from the group consisting of:

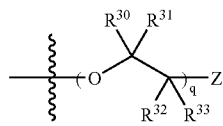

wherein q is an integer from 2 to 10; Z is —Ch;

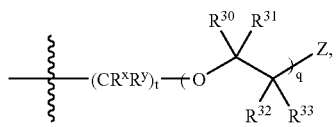

wherein q is an integer from 1 to 10, $R^x$ and $R^y$, are hydrogen, hydroxy or $C_{1-4}$ alkyl; t is 0, 1, 2 or 3; and Z, $R^{30}$, $R^{31}$, $R^{32}$ and $R^{33}$ are as described; and Z is —Ch;

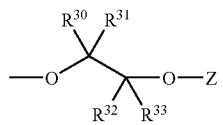

wherein Z is —Ch, $R^{30}$, $R^{31}$, $R^{32}$ and $R^{33}$ are as described above, and

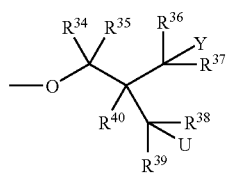

wherein Y is —Ch; U is selected from the group consisting of hydrogen, hydroxy, halogen, halogen substituted benzoyloxy, halogen substituted phenyl($C_{1-4}$)alkyl, halogen substituted aryloxy, and halogen substituted $C_{6-10}$ aryl; and $R^{34}$, $R^{35}$, $R^{36}$, $R^{37}$, $R^{38}$, $R^{39}$ and $R^{40}$ are in each instance independently selected from the group consisting of hydrogen, halogen, hydroxy, $C_{1-4}$ alkoxy, $C_{1-4}$ alkyl, and hydroxy($C_{1-4}$) alkyl;

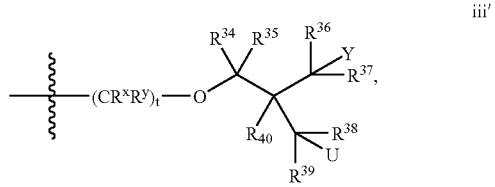

wherein, $R^x$ and $R^y$ are hydrogen, hydroxy or $C_{1-4}$ alkyl; t is 0, 1, 2 or 3; and Y, U, $R^{34}$, $R^{35}$, $R^{36}$, $R^{37}$, $R^{38}$, $R^{39}$ and $R^{40}$ are as described above;

iv. —$(CH_2)_w$—O—Ch, wherein w is an integer from 1 to 10;

v. —Ch; and vi. —$(CH_2)_w$—Ch, wherein w is an integer from 1 to 10;

wherein, the moiety "—Ch" is a chelating ligand capable of complexing with a metal to form a metal chelate. Many ligands are known in the art and are suitable for use as a labeling moiety for the compounds of the present invention. Those of skill in the art will understand that such ligands provide a way to label compounds and the invention is not limited to particular ligands, many of which are interchangeable. Preferably, this ligand is a tri- or tetradentate ligand, such as $N_3$, $N_2S$, $NS_2$, $N_4$ and those of the $N_2S_2$ type, represented by, but not limited to, the following structure:

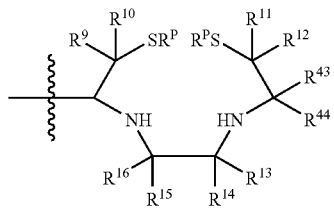

wherein $R^P$ is hydrogen or a sulfhydryl protecting group, and $R^9R^{10}$, $R^{11}$, $R^{12}$, $R^{13}$, $R^{14}$, $R^{15}$, $R^{16}$, $R^{43}$ and $R^{44}$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl. When complexed with a metal such as 99m-Tc, —Ch has the following structure:

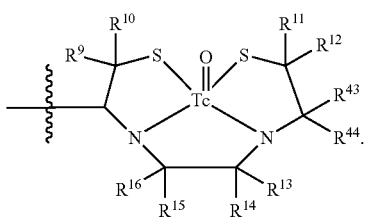

Additionally, a rhenium radioisotope can be complexed with the tetradentate ligand, rather than technetium. When the chelating moiety is not complexed with a metal, $R^P$ are both hydrogen, or can be any of the variety of protecting groups available for sulfur, including methoxymethyl, methoxyethoxymethyl, p-methoxybenzyl or benzyl. Sulfur protecting groups are described in detail in Greene, T. W. and Wuts, P. G. M., *Protective Groups in Organic Synthesis*, 2nd Edition, John Wiley and Sons, Inc., New York (1991). Protecting group $R^P$ can be removed by appropriate methods well known in the art of organic synthesis, such as trifluoroacetic acid, mercuric chloride or sodium in liquid ammonia. In the case of Lewis acid labile groups, including acetamidomethyl and benzamidomethyl, $R^P$ can be left intact. Labeling of the ligand with technetium in this case will cleave the protecting group, rendering the protected diaminedithiol equivalent to the unprotected form. Further, several ligands of the general $N_2S_2$ type are known, and can be used interchangeably without changing the scope of the invention; and $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy $(C_{1-4})$alkyl.

Preferred values of $R^1$ are hydroxy or $NR^aR^b(CH_2)_p$—, wherein p is an integer from 0 to 5, and $R^a$ and $R^b$ are independently hydrogen, $C_{1-4}$ alkyl or $(CH_2)_dX$, where X is halogen, and d is an integer from 1 to 4 Useful values of p include integers from 0 to 5. Preferably, p is 0, 1 or 2. Most preferably, p is 0 such that $R^1$ represents $NR^aR^b$. In preferred embodiments, $R^1$ is either in the meta or para position relative to the respective bridge. A preferred value of $R^1$ is $NR^aR^b$, wherein $R^a$ and $R^b$ are independently hydrogen or $C_{1-4}$ alkyl. In this embodiment, it is preferable that the $C_{1-4}$ alkyl is methyl. Preferably one of $R^a$ and $R^b$ is hydrogen, the other is $C_{1-4}$ alkyl, such as methyl or both $R^a$ and $R^b$ are methyl. Another preferred value of $R^1$ is hydroxy. Also preferred for $R^1$ are any groups that after administration into the body metabolize or degrade to the preferred values of $R^1$ listed above. Such groups are known in the art to constitute a prodrug and the groups capable of forming prodrugs are well-known to one of ordinary skill in the art.

Useful values of n include integers from 1 to 6. Preferably, the value of n is from 1 to 4. Most preferably, the value of n is from 1 to 3. It is especially preferred that n is one.

Useful values of $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy$(C_{1-4})$alkyl. The value of n determines the number of $R^7$ and $R^8$ group(s) present in the compound. If present more than once in a particular compound, in each instance of $R^7$ and $R^8$ the value can be different from any other value of $R^7$ and $R^8$. In preferred embodiments, $R^7$ and $R^8$ are each hydrogen in every instance.

Useful values of $R^2$ include substructures i, i', ii, iii and iii' as depicted above. In preferred embodiments of Formula I, $R^2$ is either in the meta or para position relative to the respective bridge. Preferably, in a compound where $R^2$ is i or i', q is an integer from 2 to 5. Most preferably, q is 3 or 4. In substructure i or i', useful values of $R^{30}$, $R^{31}$, $R^{32}$ and $R^{33}$ independently include hydrogen, hydroxy, $C_{1-4}$ alkoxy, $C_{1-4}$ alkyl, and hydroxy$(C_{1-4})$alkyl. Preferred compounds include those where one or more of $R^{30}$, $R^{31}$, $R^{32}$ and $R^{33}$ are hydrogen. More preferred compounds include those where each of $R^{30}$, $R^{31}$, $R^{32}$ and $R^{33}$ is hydrogen.

In substructure iii or iii', useful values of U and $R^{34}$, $R^{35}$, $R^{36}$, $R^{37}$, $R^{38}$, $R^{39}$ and $R^{40}$ are described above. Preferred compounds include those where U is hydroxy.

Useful compounds include those compounds where one, no more than three, of $A_1$, $A_2$, $A_3$, $A_4$ and $A_5$ is N, and the others are —CH or —$CR^2$ as permitted. It is preferred that if only one of $A_1$, $A_2$, $A_3$, $A_4$ and $A_5$ is N, that it is $A_4$.

In another aspect, the present invention is directed to a compound of Formula II, having the following structure:

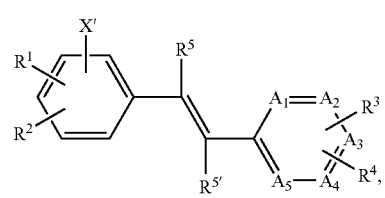

II or a pharmaceutically acceptable salt thereof, wherein: at least one, no more than three, of $A_1$, $A_2$, $A_3$, $A_4$ and $A_5$ is N, the others are —CH, —$CR^3$ or —$CR^4$ as permitted; $R^5$ and $R^{5'}$ are independently hydrogen or $C_{1-4}$ alkyl; $R^1$ and $R^2$, in each instance, is independently selected from the group consisting of hydrogen, halogen, $C_{1-4}$ alkyl, cyano, carboxy$(C_{1-5})$alkyl, trifluoromethyl, nitro, halo$(C_{1-4})$alkyl, formyl and $NR^6R^7(CH_2)_p$—, wherein p is an integer from 0 to 5, and $R^6$ and $R^7$ are independently hydrogen, $C_{1-4}$ alkyl or $(CH_2)_dX$, where X is halogen, and d is an integer from 1 to 4; in addition to the values listed above for $R^1$ and $R^2$, $R^1$ and/or $R^2$ can independently also be hydroxy; $R^3$ is selected from the group consisting of hydrogen, halogen, $C_{1-4}$ alkyl, cyano, carboxy $(C_{1-5})$alkyl, trifluoromethyl, nitro, halo$(C_{1-4})$alkyl, formyl, $NR^6R^7(CH_2)_p$—, wherein p is an integer from 0 to 5, and $R^6$ and $R^7$ are independently hydrogen, $C_{1-4}$ alkyl or $(CH_2)_dX$, where X is halogen, and d is an integer from 1 to 4, $^{18}$Fluoromethyl, $^{18}$Fluoroethyl, $^{18}$Fluoropropyl and Sn(alkyl)$_3$;

$R^4$ is selected from the group consisting of:
a. $C_{1-4}$ alkylthio,
b. $C_{1-4}$ alkylsulfonyl,
c. hydroxy,
d. $C_{1-4}$ alkoxy,
e. $NR^6R^7(CH_2)_p$—, wherein p is an integer from 0 to 5, and $R^6$ and $R^7$ are independently hydrogen, $C_{1-4}$ alkyl or $(CH_2)_dX$, where X is halogen, and d is an integer from 1 to 4,
f. phenyl$(C_{1-4})$alkyl,
g. $C_{6-10}$ aryl,
h. heteroaryl,
i. heterocycle,
j. heterocycle$(C_{1-4})$alkyl, and
k. $C_{3-6}$ cycloalkyl, wherein said phenyl$(C_{1-4})$alkyl, $C_{6-10}$ aryl, heteroaryl, heterocycle, heterocycle$(C_{1-4})$alkyl or $C_{3-6}$ cycloalkyl is substituted with one of the following: $C_{1-4}$ alkylthio, $C_{1-4}$ alkyl sulfonyl, methoxy, hydroxy, dimethylamino or methylamino; and, X' is hydrogen, $^{18}$Fluoromethyl, $^{18}$Fluoroethyl, $^{18}$Fluoropropyl, $^{125}$I, $^{123}$I, $^{131}$I, $^{18}$F, $^{76}$Br, $^{77}$Br or Sn(alkyl)$_3$; provided that one of $R^1$, $R^2$, $R^3$ or $R^4$ is $NR^6R^7(CH_2)_p$—. In another embodiment, it is also provided that one of $R^1$, $R^2$ or $R^4$ is hydroxy.

Useful values of $R^5$ and $R^{5'}$ include all the values listed above. Preferably, $R^5$ and $R^{5'}$ are independently hydrogen or a $C_{1-4}$ alkyl such as methyl. Also preferred, $R^1$ and $R^2$ are independently hydroxy, monomethylamine or dimethylamine.

Useful values of $R^3$ include all those values listed above. More preferably, $R^3$ is hydrogen, $^{18}$Fluoromethyl, $^{18}$Fluoroethyl, $^{18}$Fluoropropyl, $^{125}$I, $^{123}$I, $^{131}$I or $^{18}$F.

Useful values of $R^1$ and $R^2$ include all the values listed above. Preferably, $R^1$ and $R^2$ are independently hydrogen or a $C_{1-4}$ alkyl such as methyl.

Useful values of $R^4$ include all those values listed above. Preferably, $R^4$ is methylthio, methylsulfonyl, hydroxy, methoxy or $NR^6R^7(CH_2)_p$—.

Useful values of $X'$ include all those listed above. Preferred values include hydrogen, $^{18}$Fluoromethyl, $^{18}$Fluoroethyl or $^{18}$Fluoropropyl, $^{125}$I, $^{123}$I, $^{131}$I and $^{18}$F.

In all compounds of the present invention wherein only one of $A_1$, $A_2$, $A_3$, $A_4$ and $A_5$ is N, it is more preferred that $A_4$ is N.

Representative compounds of the present invention include:

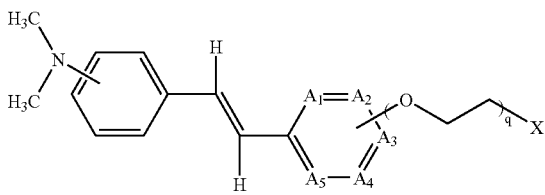

Iα

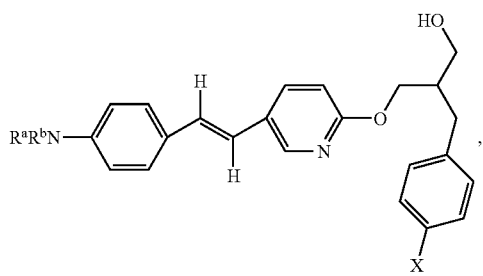

20

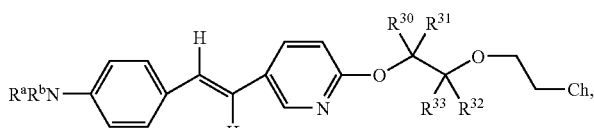

21

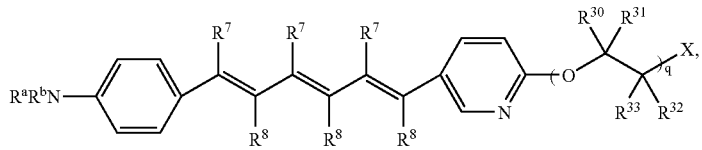

22

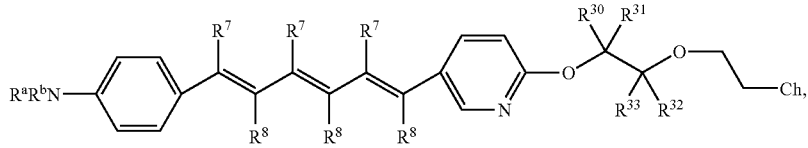

23 wherein —Ch is an $N_2S_2$ type chelating moiety, X, q, $R^a$, $R^b$, $R^7$, $R^8$, $R^{30}$, $R^{31}$, $R^{32}$ and $R^{33}$ are as described above. Most preferably, $R^a$ and $R^b$ are both methyl.

In another embodiment are compounds of Formula I'a having the following general structure:

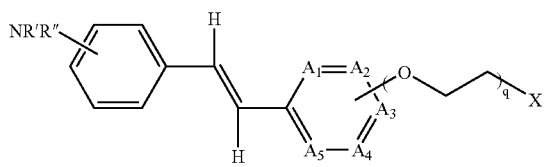

I'a wherein at least one, no more than three, of $A_1$, $A_2$, $A_3$, $A_4$ and $A_5$ is N, the others are —CH; q is an integer from 1 to 10; R' and R" are each independently hydrogen or $C_{1-4}$ alkyl and X is a radiolabeled halogen or —Ch moiety. An example of these compounds include compounds of Formula Ia having the following structure:

wherein at least one, no more than three, of $A_1$, $A_2$, $A_3$, $A_4$ and $A_5$ is N, the others are —CH; q is an integer from 1 to 10; and X is a radiolabeled halogen or —Ch moiety. Preferably, a mono or di $C_{1-4}$ alkylamino, more preferably monomethylamino or dimethylamino and PEG substituents are in the para position relative to the ethylene bridge. Also, it is preferred that $A_4$ is N, and $A_1$, $A_2$, $A_3$ and $A_5$ are each —CH. Preferred values of q are integers from 2 to 5; and especially preferred values are 3 and 4. Preferred values of X include $^{123}$I and $^{18}$F. The most preferred value of X is $^{18}$F.

In another embodiment of the present invention are compounds of Formula III having the following structure:

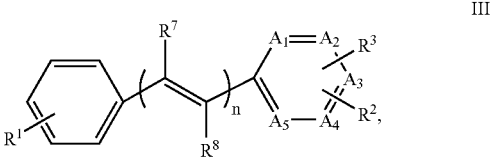

III or a pharmaceutically acceptable salt thereof; wherein, n is an integer from one to six; at least one, no more than three, of $A_1$, $A_2$, $A_3$, $A_4$ and $A_5$ is N, the others are —CH, —$CR^2$ or —$CR^3$ as permitted; $R^1$ includes all the useful values listed above under Formula I, preferably hydroxy or $NR^aR^b(CH_2)_p$—, wherein p is an integer from 0 to 5, and $R^a$ and $R^b$ are independently hydrogen, $C_{1-4}$ alkyl or $(CH_2)_dX$, where X is halogen, and d is an integer from 1 to 4, $R^3$ is selected from the group of $^{125}I$, $^{123}I$, $^{131}I$, $^{18}F$, $^{18}F(C_1-C_4)$alkyl, $^{76}Br$, $^{77}Br$ or $Sn(alkyl)_3$; $R^2$ is selected from the group consisting of:

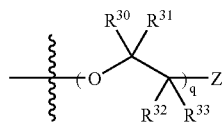

i wherein q is an integer from 1 to 10; Z is selected from the group consisting of hydrogen, hydroxy, halogen, $C_{1-4}$ alkoxy, $C_{1-4}$ alkyl, and hydroxy($C_{1-4}$)alkyl; and $R^{30}$, $R^{31}$, $R^{32}$ and $R^{33}$ are in each instance independently selected from the group consisting of hydrogen, hydroxy, $C_{1-4}$ alkoxy, $C_{1-4}$ alkyl, and hydroxy($C_{1-4}$)alkyl;

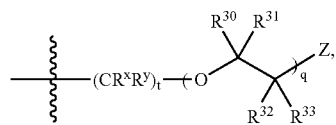

i'

Wherein q is an integer from 1 to 10, $R^x$ and $R^y$ are hydrogen, hydroxy or $C_{1-4}$ alkyl; t is 0, 1, 2 or 3; and Z, $R^{30}$, $R^{31}$, $R^{32}$ and $R^{33}$ are as described;

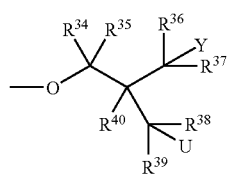

ii wherein Y and U are independently selected from the group consisting of hydrogen, hydroxyl, halogen, $C_{1-4}$ alkoxy, $C_{1-4}$ alkyl, and hydroxy($C_{1-4}$)alkyl; U is selected from the group consisting of hydrogen, hydroxy, halogen, halogen substituted benzoyloxy, halogen substituted phenyl($C_{1-4}$)alkyl, halogen substituted aryloxy, and halogen substituted $C_{6-10}$ aryl; and $R^{34}$, $R^{35}$, $R^{36}$, $R^{37}$, $R^{38}$, $R^{39}$ and $R^{40}$ are in each instance independently selected from the group consisting of hydrogen, halogen, hydroxy, $C_{1-4}$ alkoxy, $C_{1-4}$ alkyl, and hydroxy($C_{1-4}$)alkyl;

ii' wherein $R^x$ and $R^y$ are hydrogen, hydroxy or $C_{1-4}$ alkyl; t is 0, 1, 2 or 3; and Y, U, $R^{34}$, $R^{35}$, $R^{36}$, $R^{37}$, $R^{38}$, $R^{39}$ and $R^{40}$ are as described above;

iii. NR'R", wherein at least one of R' and R" is $(CH_2)_dX$, where X is halogen, preferably F or $^{18}F$, and d is an integer from 1 to 4; the other of R' and R" is selected from the group consisting of hydrogen, $C_{1-4}$ alkyl, halo($C_{1-4}$)alkyl, and hydroxy($C_{1-4}$)alkyl;

iv. NR'R"—($C_{1-4}$)alkyl, wherein at least one of R' and R" is $(CH_2)_dX$, where X is halogen, preferably F or $^{18}F$, and d is an integer from 1 to 4; the other of R' and R" is selected from the group consisting of hydrogen, $C_{1-4}$ alkyl, halo($C_{1-4}$)alkyl, and hydroxy($C_{1-4}$)alkyl;

v. halo($C_{1-4}$)alkyl; and vi. an ether (R—O—R) having the following structure: [halo($C_{1-4}$)alkyl-O—($C_{1-4}$)alkyl]-; and $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl.

Preferred compounds include those where the halogen, in one or more occurrence on the structure, is a radiolabeled halogen. Also preferred are compounds wherein the halogen is selected from the group consisting of I, $^{123}I$, $^{125}I$, $^{131}I$, Br, $^{76}Br$, $^{77}Br$, F or $^{18}F$. Especially preferred compounds are those that contain $^{18}F$. Compounds containing $^{123}I$ are also especially preferred.

Useful values of $R^1$ are listed above. Preferred values are hydroxy or $NR^aR^b(CH_2)_p$—, wherein p is an integer from 0 to 5, and $R^a$ and $R^b$ are independently hydrogen, $C_{1-4}$ alkyl or $(CH_2)_dX$, where X is halogen, and d is an integer from 1 to 4 Useful values of p include integers from 0 to 5. Preferably, p is 0, 1 or 2. Most preferably, p is 0 such that $R^1$ represents $NR^aR^b$. In preferred embodiments, $R^1$ is either in the meta or para position relative to the respective bridge. A preferred value of $R^1$ is $NR^aR^b$, wherein $R^a$ and $R^b$ are independently hydrogen or $C_{1-4}$ alkyl. In this embodiment, it is preferable that the $C_{1-4}$ alkyl is methyl. Preferably one of $R^a$ and $R^b$ is hydrogen, the other is $C_{1-4}$ alkyl, such as methyl. Most preferably, both $R^a$ and $R^b$ are methyl. Another preferred value of $R^1$ is hydroxy. Also preferred for $R^1$ are any groups that after administration into the body metabolize or degrade to the preferred values of $R^1$ listed above. Such groups are known in the art to constitute a prodrug and the groups capable of forming prodrugs are well-known to one of ordinary skill in the art.

Useful values of n include integers from 1 to 6. Preferably, the value of n is from 1 to 4. Most preferably, the value of n is from 1 to 3. It is especially preferred that n is one.

Useful values of $R^7$ and $R^8$ are in each instance independently selected from the group consisting of hydrogen, hydroxy, amino, methylamino, dimethylamino, $C_{1-4}$ alkoxy, $C_{1-4}$ alkyl, and hydroxy($C_{1-4}$)alkyl. The value of n determines the number of $R^7$ and $R^8$ group(s) present in the compound. If present more than once in a particular compound, in each instance of $R^7$ and $R^8$ the value can be different from any other value of $R^7$ and $R^8$. In preferred embodiments, $R^7$ and $R^8$ are each hydrogen in every instance.

wherein $R^a$ and $R^b$ are independently selected from hydrogen or $C_1$-$C_4$ alkyl and q is an integer from 1 to 4 and $R^3$ is preferably $^{123}I$ or $^{18}F$;

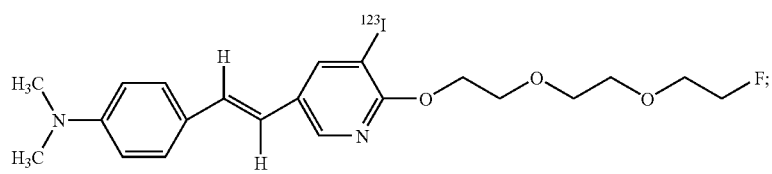

13a

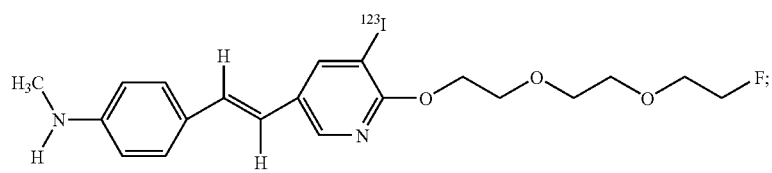

13b

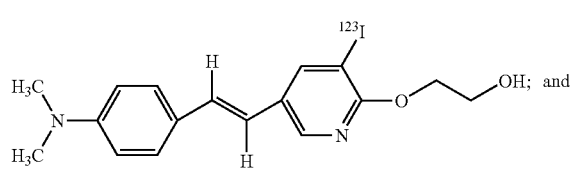

16a

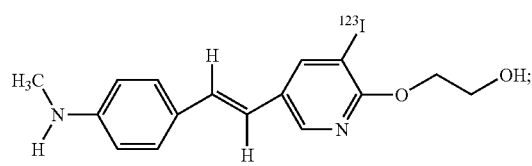

16b

Useful values of $R^2$ include substructures i, i', ii, ii', iii, iv, v, and vi, as depicted above. In preferred embodiments of Formula I, $R^2$ is either in the meta or para position relative to the respective bridge. Preferably, $R^2$ is substructure i or ii. Also preferred are substructures i' and ii'. In these embodiments, useful values of q include integers from one to ten. Preferably, in a compound where $R^2$ is i or i', q is an integer from 1 to 5. Most preferably, q is 1 to 4, especially 3 or 4. In substructure i or i', useful values of $R^{30}$, $R^{31}$, $R^{32}$ and $R^{33}$ independently include hydrogen, hydroxy, $C_{1-4}$ alkoxy, $C_{1-4}$ alkyl, and hydroxy($C_{1-4}$)alkyl. Preferred compounds include those where one or more of $R^{30}$, $R^{31}$, $R^{32}$ and $R^{33}$ are hydrogen. More preferred compounds include those where each of $R^{30}$, $R^{31}$, $R^{32}$ and $R^{33}$ is hydrogen.

In substructure ii or ii', useful values of Y, U and $R^{34}$, $R^{35}$, $R^{36}$, $R^{37}$, $R^{38}$, $R^{39}$ and $R^{40}$ are described above. Preferred compounds include those where U is hydroxy.

Useful compounds include those compounds where at least one, no more than three, of $A_1$, $A_2$, $A_3$, $A_4$ and $A_5$ is N, and the others are —CH or —$CR^2$ as permitted. It is more preferred that N be in position $A_4$.

Particularly useful compounds of Formula III include those compounds where $A_4$ is N, and the others are —CH, —$CR^2$ or —$CR^3$ as permitted.

Especially preferred compounds of Formula III wherein $A_4$ is N, include the following:

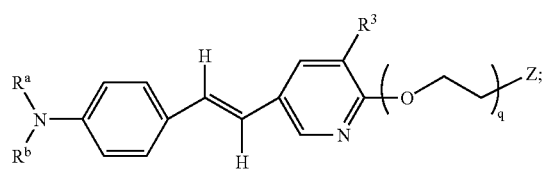

Examples of most preferred compounds of Formula III include the following:

Other preferred compounds of Formula III, when $R^2$ is ii, include:

17a

18a wherein Y is selected from the group consisting of hydrogen and F.

Compounds of Formula III when $R^2$ is i, or i' when t is 0, include hydroxy ethers such as:

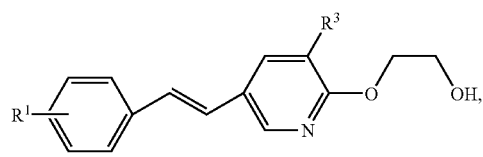

wherein $R^1$ and $R^3$ are as described above under Formula III.

In all embodiments of Formulae I and III containing —$(CR^xR^y)_t$ where t is other than zero, the compounds have the following general structure wherein there is at least one carbon-carbon bond between a substituent and the nitrogen-containing ring:

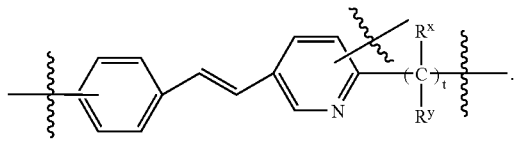

The compounds of the present invention can also contain a radioactive isotope of carbon as the radiolabel. This refers to a compound that comprises one or more radioactive carbon atoms, preferably $^{11}C$, with a specific activity above that of the background level for that atom. It is well known, in this respect, that naturally occurring elements are present in the form of varying isotopes, some of which are radioactive isotopes. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The composition claimed herein comprising a carbon-labeled compound(s) of the present invention will have an amount of the compound such that the composition can be used for tracing, imaging, radiotherapy, and the like.

In certain embodiments of the compounds disclosed herein, a halogen, preferably $^{18}F$, or a chelating agent is linked to the styrylpyridine backbone through a PEG chain, having a variable number of ethoxy groups. The fluorinated styrylpyridine, 2, displayed high binding affinity (Ki=2.5±0.4 nM). The dimethylamino analog showed the greatest affinity. This is in contrast to stilbene analogs, which tend to possess higher affinity when monomethylamino substituted. As shown in Schemes 1-3 herein, radiolabeling was successfully performed giving the target compounds. The synthesis of compound 2 in Scheme 5 resulted in a preparation time of about 60 mins; radiochemical yield of ~35% (decay corrected); radiochemical purity of >98%; and specific activity of from about 1,000 to about 1,500 Ci/mmol. In vivo biodistribution of a $^{18}F$ pegylated styrylpyridine in normal mice exhibited excellent brain penetrations and rapid washouts after an iv injection. Autoradiography of postmortem AD brain sections of 2 confirmed the specific binding related to the presence of Aβ plaques.

Preferable values under the scope of $C_{6-10}$ aryl include phenyl, naphthyl or tetrahydronaphthyl. Preferable values of under the scope of heteroaryl include thienyl, furyl, pyranyl, pyrrolyl, pyridinyl, indolyl, and imidazolyl. Preferable values under the scope of heterocycle include piperidinyl, pyrrolidinyl, and morpholinyl. A preferred embodiment of a $C_{6-10}$ aryl, heteroaryl, heterocycle, heterocycle($C_{1-4}$)alkyl or $C_{3-6}$ cycloalkyl, contains a ring substituted with one of the following: $C_{1-4}$ alkylthio, $C_{1-4}$ alkyl sulfonyl, methoxy, hydroxy, dimethylamino or methylamino.

The compounds of Formulae I, Ia, II, and III may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

When any variable occurs more than one time in any constituent or in Formula I, Ia, II or III its definition on each occurrence is independent of its definition at every other occurrence. Also combinations of substituents and/or variables are permissible only if such combinations result in stable compounds.

The term "alkyl" as employed herein by itself or as part of another group refers to both straight and branched chain radicals of up to 8 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length.

The term "monoalkylamine" as employed herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" or "halogen" employed herein by itself or as part of another group refers to chlorine, bromine, fluorine or iodine and their isotopes. The term "radiohalogen" refers specifically to radioactive halogen isotopes.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "alkylthio" as employed herein by itself or as part of another group refers to a thioether of the structure: R—S, wherein R is a $C_{1-4}$ alkyl as defined above.

The term "alkylsulfonyl" as employed herein by itself or as part of another group refers to a sulfone of the structure: R—$SO_2$, wherein R is a $C_{1-4}$ alkyl as defined above.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of such heterocyclic groups include piperidinyl, pyrrolyl, pyrrolidinyl, imidazolyl, imidazinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl, and morpholinyl.

The term "heteroatom" is used herein to mean an oxygen atom ("O"), a sulfur atom ("S") or a nitrogen atom ("N"). It will be recognized that when the heteroatom is nitrogen, it may form an NRR moiety, wherein the R groups independently from one another may be hydrogen or $C_{1-4}$ alkyl, $C_{2-4}$ aminoalkyl, $C_{1-4}$ halo alkyl, halo benzyl, or $R^1$ and $R^2$ are taken together to form a 5- to 7-member heterocyclic ring optionally having O, S or $NR^c$ in said ring, where $R^c$ is hydrogen or $C_{1-4}$ alkyl.

The term "heteroaryl" as employed herein refers to groups having 5 to 14 ring atoms; 6, 10 or 14 π electrons shared in a cyclic array; and containing carbon atoms and 1, 2, 3 or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, α, β, or γ-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

Another aspect of this invention is related to methods of preparing compounds of Formulae I, Ia, II and III.

The synthesis of dimethylamino substituted styrylpyridine derivative 1 and its fluoropegylated compound 2 is shown in scheme 1. Compound 1 was obtained by a Wittig reaction between diethyl 4-(dimethylamino)benzylphosphonate and 6-chloronicotinaldehyde at the present of potassium tert-butoxide in DMF (yield 62%). A direct alkylation of compound 1 with 2-(2-(2-fluoroethoxy)ethoxy)ethanol[2] using sodium hydride in THF obtained the fluoropegylated compound 2 (yield 33%), which can be used as the cold standard for the radio-labeling. The preparation of monomethylamino substituted derivative 6 was accomplished through a route showing in Scheme 2. A Wittig reaction between 4-nitro-benzylphosphonate and 6-chloronicotinaldehyde at the present of sodium methoxide in methanol under refluxing condition obtained compound 3 in a high yield (88%). Compound 3 can be easily filtered out after the reaction and used directly for next step; no further purification is required. The alkylation of 3 with 2-(2-(2-fluoroethoxy)ethoxy)ethanol using sodium hydride in THF obtained compound 4 (yield 30%). The nitro group of compound 4 was reduced using stannous chloride in ethanol to obtain compound 5 (yield 58%). Monomethylation of 5 was achieved using paraformaldehyde, sodium methoxide and sodium borohydride to obtain compound 6 in a relatively high yield (73%).

To make desired F-18 labeled dimethylamino substituted styrylpyridine derivative [$^{18}$F]2, the tosylate 10 (Scheme 3) was used as the precursor. The preparation of 10 started with a microwave-assisted alkylation of 3 with triethylene glycol in DMF to obtain compound 7 (yield 77%). The nitro group of 7 was then reduced to amine using stannous chloride to give compound 8 (yield 76%) then followed by a dimethylation using paraformaldehyde, sodium cyanoborohydride in acetic acid to obtain compound 9 in a high yield (95%). Mesylation of 9 was tried first, however, the mesylate of 9 was very unstable and decomposed during the preparation. Tosylation of 9 was accomplished successfully using tosylchloride in pyridine to give desired tosylate 10 (yield 41%) as the precursor for making radio-labeled [$^{18}$F]2.

SCHEME 1

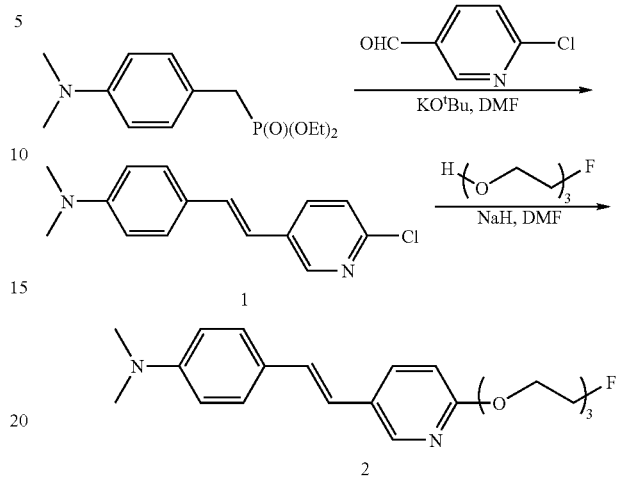

SCHEME 2

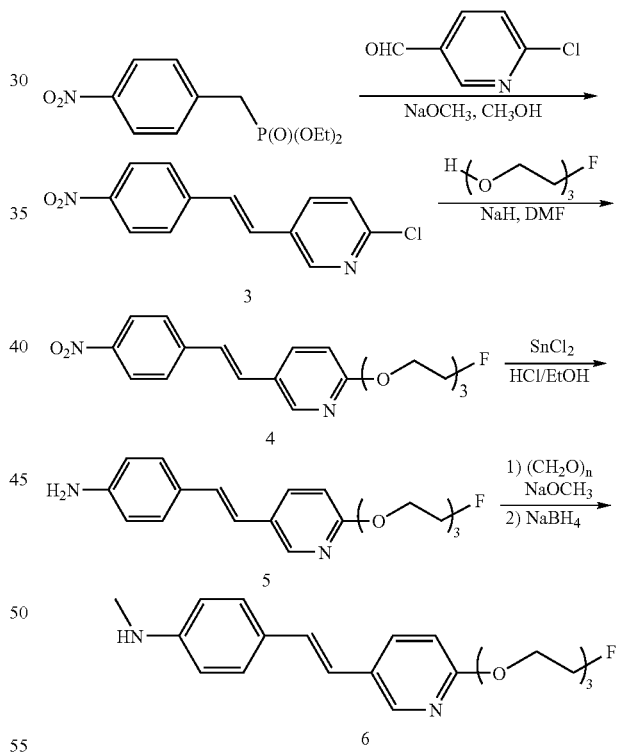

SCHEME 3

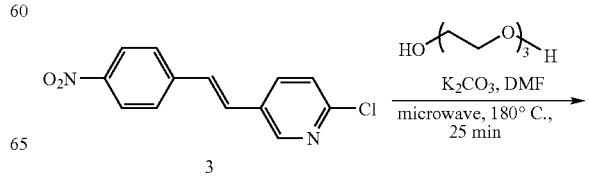

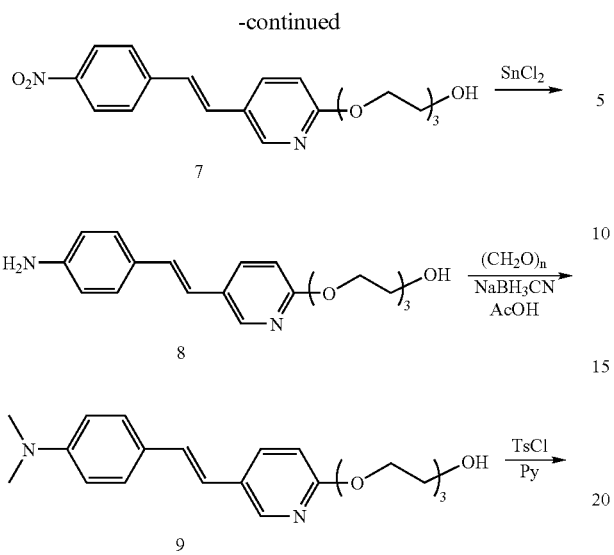

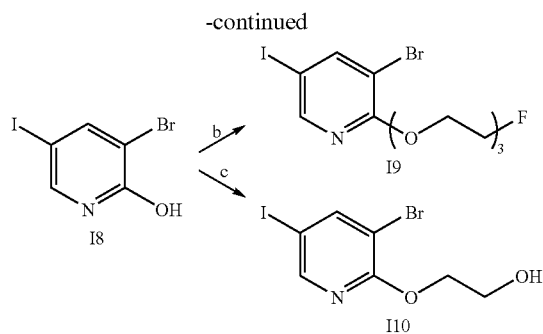

Reagents and conditions: (a) NIS, CH$_3$CN, reflux, 1 h, (b) F(CH$_2$CH$_2$O)$_3$H, Ph$_3$P, DIAD, THF, -5° C. to rt, 2 h, (c) (1) HOCH$_2$CH$_2$OTBDMS, Ph$_3$P, DIAD, THF, -5° C. to rt, 2 h; (2) 1% HCl in 95% EtOH, rt, 1 h.

SCHEME 6

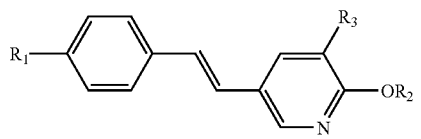

11: R$_2$ = —(CH$_2$CH$_2$O)$_2$CH$_2$CH$_2$F, R$_3$ = —Br
12: R$_2$ = —(CH$_2$CH$_2$O)$_2$CH$_2$CH$_2$F, R$_3$ = —SnBu$_3$
13: R$_2$ = —(CH$_2$CH$_2$O)$_2$CH$_2$CH$_2$F, R$_3$ = —I
14: R$_2$ = —CH$_2$CH$_2$OH, R$_3$ = —Br
15: R$_2$ = —CH$_2$CH$_2$OH, R$_3$ = —SnBu$_3$
16: R$_2$ = —CH$_2$CH$_2$OH, R$_3$ = —I
 a: R$_1$ = —N(CH$_3$)$_2$
 b: R$_1$ = —NH(CH$_3$)
 c: R$_1$ = —N(Boc)(CH$_3$)
 d: R$_1$ = —OCOCH$_3$
 e: R$_1$ = —OH

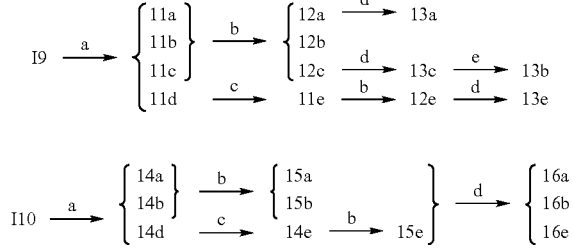

Reagents and conditions: (a) 4-substituted styrenes, K$_2$CO$_3$, Bu$_4$NBr, Pd(OAc)$_2$, DMF, 55-65° C.; (b) (Bu$_3$Sn)$_2$, Pd(PPh$_3$)$_4$, toluene, 110° C.; (c) K$_2$CO$_3$, EtOH/THF, rt, 2 h; (d) I$_2$, THF, 0° C. to rt; (e) TMSOTf, 2,6-lutidine, DCM, -78° C. to rt.

SCHEME 4

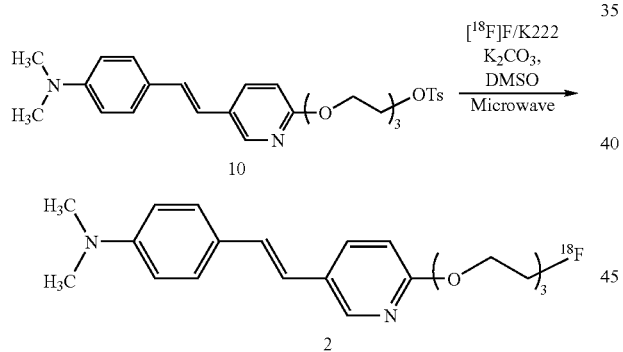

Schemes 5-7 depict a synthetic route for compounds of Formula III. Scheme 5 depicts a synthesis of several intermediates useful for preparing the compounds of the invention. Scheme 6 and 7 depict the synthesis of radiolabeled and non-radiolabeled compounds of the invention. In compounds I7-I10, "I" in the compound name means "intermediate."

SCHEME 5

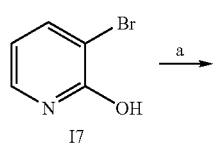

SCHEME 7

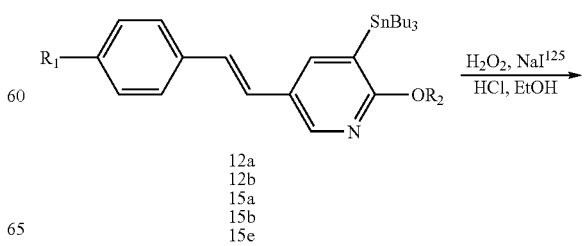

12a
12b
15a
15b
15e

-continued

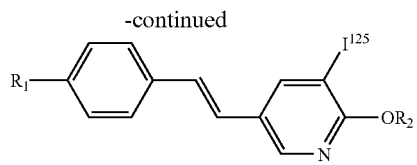

[$^{125}$I]13a: $R_1 =$ —N(CH$_3$)$_2$, $R_2 =$ —(CH$_2$CH$_2$O)$_2$CH$_2$CH$_2$F
[$^{125}$I]13b: $R_1 =$ —NH(CH$_3$), $R_2 =$ —(CH$_2$CH$_2$O)$_2$CH$_2$CH$_2$F
[$^{125}$I]16a: $R_1 =$ —N(CH$_3$)$_2$, $R_2 =$ —CH$_2$CH$_2$OH
[$^{125}$I]16b: $R_1 =$ —NH(CH$_3$), $R_2 =$ —CH$_2$CH$_2$OH
[$^{125}$I]16e: $R_1 =$ —OH, $R_2 =$ —CH$_2$CH$_2$OH

Tc-99m complexes can be prepared as follows. A small amount of non-radiolabeled compound (1-2 mg) is dissolved in 100 μL EtOH and mixed with 200 μL HCl (1 N) and 1 mL Sn-glucoheptonate solution (containing 8-32 μg SnCl$_2$ and 80-320 μg Na-glucoheptonate, pH 6.67) and 50 μL EDTA solution (0.1 N). [$^{99m}$Tc]Pertechnetate (100-200 μL; ranging from 2-20 mCi) saline solution are then added. The reaction is heated for 30 min at 100E C, then cooled to room temperature. The reaction mixture is analyzed on TLC (EtOH:conc. NH$_3$ 9:1) for product formation and purity check. The mixture can be neutralized with phosphate buffer to pH 5.0.

The present invention further relates to a method of preparing a technetium-99m complex according to the present invention by reacting technetium-99m in the form of a pertechnetate in the presence of a reducing agent and optionally a suitable chelator with an appropriate Ch-containing compound.

The reducing agent serves to reduce the Tc-99m pertechnetate which is eluted from a molybdenum-technetium generator in a physiological saline solution. Suitable reducing agents are, for example, dithionite, formamidine sulphinic acid, diaminoethane disulphinate or suitable metallic reducing agents such as Sn(II), Fe(II), Cu(I), Ti(III) or Sb(III). Sn(II) has proven to be particularly suitable.

For the above-mentioned complex-forming reaction, technetium-99m is reacted with an appropriate compound of the invention as a salt or in the form of technetium bound to comparatively weak chelators. In the latter case the desired technetium-99m complex is formed by ligand exchange. Examples of suitable chelators for the radionuclide are dicarboxylic acids, such as oxalic acid, malonic acid, succinic acid, maleic acid, orthophtalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because a chelate of technetium-99m with one of these chelators undergoes the desired ligand exchange particularly easily.

The most commonly used procedure for preparing [Tc$^V$O]$^{+3}$N$_2$S$_2$ complexes is based on stannous (II) chloride reduction of [$^{99m}$Tc]pertechnetate, the common starting material. The labeling procedure normally relies on a Tc-99m ligand exchange reaction between Tc-99m (Sn)-glucoheptonate and the N$_2$S$_2$ ligand. Preparation of stannous (II) chloride and preserving it in a consistent stannous (II) form is critically important for the success of the labeling reaction. To stabilize the air-sensitive stannous ion it is a common practice in nuclear medicine to use a lyophilized kit, in which the stannous ion is in a lyophilized powder form mixed with an excess amount of glucoheptonate under an inert gas like nitrogen or argon. The preparation of the lyophilized stannous chloride/sodium glucoheptonate kits ensures that the labeling reaction is reproducible and predictable. The N$_2$S$_2$ ligands are usually air-sensitive (thiols are easily oxidized by air) and there are subsequent reactions which lead to decomposition of the ligands. The most convenient and predictable method to preserve the ligands is to produce lyophilized kits containing 100-500 μg of the ligands under argon or nitrogen.

When the compounds of this invention are to be used as imaging agents, they must be labeled with suitable radioactive halogen isotopes. Although $^{125}$I-isotopes are useful for laboratory testing, they will generally not be useful for actual diagnostic purposes because of the relatively long half-life (60 days) and low gamma-emission (30-65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours). Suitable bromine isotopes include $^{77}$Br and $^{76}$Br.

The radiohalogenated compounds of this invention lend themselves easily to formation from materials which could be provided to users in kits. Kits for forming the imaging agents can contain, for example, a vial containing a physiologically suitable solution of an intermediate of Formula I, Ia, II or III in a concentration and at a pH suitable for optimal complexing conditions. The user would add to the vial an appropriate quantity of the radioisotope, e.g., Na$^{123}$I, and an oxidant, such as hydrogen peroxide. The resulting labeled ligand may then be administered intravenously to a patient, and receptors in the brain imaged by means of measuring the gamma ray or photo emissions therefrom.

Since the radiopharmaceutical composition according to the present invention can be prepared easily and simply, the preparation can be carried out readily by the user. Therefore, the present invention also relates to a kit, comprising:

(1) A non-radiolabeled compound of the invention, the compound optionally being in a dry condition; and also optionally having an inert, pharmaceutically acceptable carrier and/or auxiliary substances added thereto; and (2) a reducing agent and optionally a chelator;

wherein ingredients (1) and (2) may optionally be combined; and further wherein instructions for use with a prescription for carrying out the above-described method by reacting ingredients (1) and (2) with technetium-99m in the form of a pertechnetate solution may be optionally included.

Examples of suitable reducing agents and chelators for the above kit have been listed above. The pertechnetate solution can be obtained by the user from a molybdenum-technetium generator. Such generators are available in a number of institutions that perform radiodiagnostic procedures. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

When desired, the radioactive diagnostic agent may contain any additive such as pH controlling agents (e.g., acids, bases, buffers), stabilizers (e.g., ascorbic acid) or isotonizing agents (e.g., sodium chloride).

The term "pharmaceutically acceptable salt" as used herein refers to those carboxylate salts or acid addition salts of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977) which is incorporated herein by reference.)

In the first step of the present method of imaging, a labeled compound of Formula I, Ia, II or III is introduced into a tissue or a patient in a detectable quantity. The compound is typically part of a pharmaceutical composition and is administered to the tissue or the patient by methods well known to those skilled in the art.

The administration of the labeled compound to a patient can be by a general or local administration route. For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray. The labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient. One of the most desirable characteristics of an in vivo imaging agent of the brain is the ability to cross the intact blood-brain barrier after a bolus iv injection.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a radiolabeled compound of Formula I, Ia, II or III is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I, Ia, II or III is introduced into the tissue sample. After a sufficient amount of time for the compound to become bound to amyloid deposits, the compound is detected.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I, Ia, II or III into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}$C or $^{18}$F.

The radioactive diagnostic agent should have sufficient radioactivity and radioactivity concentration which can assure reliable diagnosis. For instance, in case of the radioactive metal being technetium-99m, it may be included usually in an amount of 0.1 to 50 mCi in about 0.5 to 5.0 ml at the time of administration. The amount of a compound of Formula I, Ia, II or III may be such as sufficient to form a stable chelate compound with the radioactive metal.

The thus formed chelate compound as a radioactive diagnostic agent is sufficiently stable, and therefore it may be immediately administered as such or stored until its use. When desired, the radioactive diagnostic agent may contain any additive such as pH controlling agents (e.g., acids, bases, buffers), stabilizers (e.g., ascorbic acid) or isotonizing agents (e.g., sodium chloride).

The imaging of amyloid deposits can also be carried out quantitatively so that the amount of amyloid deposits can be determined.

Preferred compounds for imaging include a radioisotope such as $^{11}$C, $^{123}$I, $^{125}$I, $^{131}$I, $^{18}$F, $^{76}$Br or $^{77}$Br.

Another aspect of the invention is a method of inhibiting amyloid plaque aggregation. The present invention also provides a method of inhibiting the aggregation of amyloid proteins to form amyloid deposits, by administering to a patient an amyloid inhibiting amount of a compound of the above Formula I, Ia, II or III.

Those skilled in the art are readily able to determine an amyloid inhibiting amount by simply administering a compound of Formula I, Ia, II or III to a patient in increasing amounts until the growth of amyloid deposits is decreased or stopped. The rate of growth can be assessed using imaging as described above or by taking a tissue sample from a patient and observing the amyloid deposits therein. The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

All reagents used in synthesis were commercial products and were used without further purification unless otherwise indicated. $^1$H NMR spectra were obtained on a Bruker DPX spectrometer (200 MHz) in CDCl$_3$. Chemical shifts are reported as δ values (parts per million) relative to internal TMS. Coupling constants are reported in hertz. The multiplicity is defined by s (singlet), d (doublet), t (triplet), br (broad), m (multiplet). Elemental analyses were performed by Atlantic Microlab INC. For each procedure, "standard workup" refers to the following steps: addition of indicated organic solvent, washing the organic layer with water then brine, separation of the organic layer from the aqueous layer, drying off the combined the organic layers with anhydrous sodium sulfate, filtering off the sodium sulfate and removing the organic solvent under reduced pressure.

EXAMPLES

Example 1

Synthesis of Compound 2

(E)-2-chloro-5-(4-dimethylaminostyryl)pyridine (1)

Potassium tert-butoxide (99 mg, 0.89 mmol) was added to a solution of diethyl-(4-dimethylamino-benzyl)-phosphonate (80 mg, 0.30 mmol) in anhydrous DMF (5.0 ml) at 0° C. 2-Chloro-5-pyridyl aldehyde (42 mg, 0.30 mmol) was then added. The reaction mixture was warmed to room temperature and stirred for 4 h. Water was added and mixture was extracted with MeOH/DCM (1:9, v/v). Organic layer was separated, washed with brine, dried over sodium sulfate and evaporated. The residue was purified by PTLC (20% Hexanes in DCM as developing solvent) to give product 1 (48 mg, Yield: 62%). $^1$H NMR (200 MHz, CDCl$_3$): δ.8.42 (1H, d, J=2.2 Hz), 7.77 (1H, d, d, J=8.4 Hz, J$_2$=2.4 Hz), 7.41 (2H, d, J=8.6 Hz), 7.27 (1H, d, J=8.2 Hz), 7.08 (1H, d, J=16.4 Hz), 6.77 (3H, m), HRMS (EI) m/z calcd. for [C$_{13}$H$_9$ClN$_2$O$_2$]$^+$ 260.0353.

(E)-2-(2-(2-(2-fluoroethoxy)ethoxy)ethoxy)-5-(4-dimethylaminostyryl)pyridine (2)

Sodium hydride (95%, 10 mg, 0.39 mmol) was added to a solution of 2-(2-(2-fluoroethoxy)ethoxy)ethanol (39 mg, 0.26 mmol) in anhydrous DMF (5.0 ml). After stirring at room temperature for 20 min, compound 5 (35 mg, 0.13 mmol) was added and reaction mixture was heated to 100° C. for 2 h. After cooling down to room temperature, water was added and the reaction mixture was extracted with ethyl acetate. Organic layer was separated, washed with brine, dried over anhydrous sodium sulfate, and evaporated. The residue was purified by PTLC (4% MeOH in DCM as developing solvent) to give product 2 (16 mg, Yield; 32.9%): $^1$H NMR (200 MHz, CDCl$_3$): δ.8.14 (1H, d, J=2.4 Hz), 7.76 (1H, d, d, J=8.6 Hz, J$_2$=2.4 Hz), 7.39 (2H, d, J=8.8 Hz), 6.87 (2H, m), 6.76 (3H, m), 4.53 (2H, d, t, J$_1$=47.6 Hz, J$_2$=4.2 Hz), 4.50 (2H, t, J=4.8 Hz), 3.85 (3H, m), 3.70 (5H, m), 2.99 (6H, s). HRMS (EI) m/z calcd. for [C$_{21}$H$_{28}$N$_2$O$_4$]$^+$ 372.2049.

Example 2

Synthesis of Compound 6

(E)-2-chloro-5-(4-nitrostyryl)pyridine (3)

Sodium methoxide (1 M in methanol, 5.0 ml) was added slowly into a solution of diethyl-(4-nitro-benzyl)-phosphonate (546 mg, 2.0 mmol) and 2-chloro-5-pyridyl aldehyde (283 mg, 2.0 mmol) in methanol (5.0 ml). The reaction mixture was then refluxed for 1 h. After cooled down to 0° C., yellow precipitate was filtered and washed with cold methanol to obtain product 3 (458 mg, Yield: 88%), which was used directly for next step without further purification. 3: $^1$H NMR (200 MHz, CDCl$_3$): δ.8.53 (1H, d, J=2.4 Hz), 8.25 (2H, d, J=8.8 Hz), 7.85 (1H, d, d, J=8.4 Hz, J$_2$=2.4 Hz), 7.65 (2H, d, J=8.8 Hz), 7.36 (1H, d, J=8.4 Hz), 7.19 (2H, s), HRMS (EI) m/z calcd. for [C$_{13}$H$_9$ClN$_2$O$_2$]$^+$ 260.0353.

(E)-2-(2-(2-(2-fluoroethoxy)ethoxy)ethoxy)-5-(4-nitrostyryl)pyridine (4)

Under the protection of nitrogen atmosphere, 2-(2-(2-fluoroethoxy)ethoxy)-ethanol$^a$ (60 mg, 0.39 mmol) was added into a mixture of sodium hydride (26.4 mg, 60% dispersion in mineral oil, 0.66 mmol) in anhydrous DMF (5 ml) at 0° C. The mixture was stirred at room temperature for half an hour and compound 3 (85.7 mg, 0.33 mmol) was added. The reaction mixture was then heated to 100° C. for 2 hours and cooled down. Ethyl acetate and water was added, organic layer was separated, washed with brine, dried over anhydrous sodium sulfate and evaporated. The residue was purified by PTLC (2% MeOH in DCM as developing solvent) to give product 4 (37 mg, Yield: 30%): $^1$H NMR (200 MHz, CDCl$_3$): δ.8.22 (3H, d, J=8.8 Hz), 7.84 (1H, d, d, J=8.6 Hz, J$_2$=2.4 Hz), 7.61 (2H, d, J=8.8 Hz), 7.20 (1H, d, J=16.4 Hz), 7.02 (1H, d, J=16.4 Hz), 6.84 (1H, d, J=8.6 Hz), 4.53 (2H, d, t, J=47.6 Hz, J$_2$=4.2 Hz), 4.52 (2H, t, J=4.8 Hz), 3.85 (3H, m), 3.70 (5H, m); HRMS (EI) m/z calcd. for [C$_{19}$H$_{21}$FN$_2$O$_5$]$^+$ 376.1435.

(E)-2-(2-(2-(2-fluoroethoxy)ethoxy)ethoxy)-5-(4-aminostyryl)pyridine (5)

Compound 4 (34 mg, 0.09 mmol) was dissolved in ethanol (5 ml) followed by the addition of stannous chloride (51.4 mg, 0.27 mmol) and concentrated HCl (0.25 ml). The reaction mixture was refluxed for 2 hours and cooled down. 2N NaOH was used to adjust pH to 10. Dichloromethane was added and the organic layer was separated, washed with brine, dried over anhydrous sodium sulfate and evaporated. The residue was purified by PTLC (3% MeOH in DCM as developing solvent) to give product 5 (18 mg, Yield: 58%): $^1$H NMR (200 MHz, CDCl$_3$): δ.8.14 (1H, d, J=2.2 Hz), 7.76 (1H, d, d, J=8.6 Hz, J$_2$=2.4 Hz), 7.32 (2H, d, J=8.4 Hz), 6.80 (5H, m), 4.53 (2H, d, t, J$_1$=47.6 Hz, J$_2$=4.2 Hz), 4.49 (2H, t, J=4.8 Hz), 3.85 (3H, m), 3.70 (5H, m), 1.8-3.0 (2H, br); HRMS (EI) m/z calcd. for [C$_{19}$H$_{23}$FN$_2$O$_3$]$^+$ 376.1693.

(E)-2-(2-(2-(2-fluoroethoxy)ethoxy)ethoxy)-5-(4-methylaminostyryl)pyridine (6)

Sodium methoxide (1M in methanol, 0.23 ml) was added to a solution of compound 5 (15.8 mg, 0.046 mmol) in methanol (5 ml) followed by the addition of paraformaldehyde (6.6 mg, 0.23 mmol). The reaction mixture was refluxed for 1.5 hour then cooled to 0° C. with an ice bath. Sodium borohydride (10.4 mg, 0.27 mmol) was added with caution. The mixture was refluxed again for 1 hour and cooled down. Dichloromethane and water was added. Organic layer was separated, washed with brine, dried over anhydrous sodium sulfate and evaporated. The residue was purified by PTLC (3% MeOH in DCM as developing solvent) to give product 6 (12 mg, Yield: 73%): $^1$H NMR (200 MHz, CDCl$_3$): δ.8.14 (1H, d, J=2.2 Hz), 7.76 (1H, d, d, J=8.6 Hz, J$_2$=2.4 Hz), 7.35 (2H, d, J=8.6 Hz), 6.92 (1H, d, J=16.4 Hz), 6.80 (1H, d, J=16.4 Hz), 6.76 (2H, d, J=8.6 Hz), 4.53 (2H, d, t, J$_1$=47.6 Hz, J$_2$=4.2 Hz), 4.49 (2H, t, J=4.8 Hz), 3.85 (3H, m), 3.70 (5H, m), 2.88 (3H, s). HRMS (EI) m/z calcd. for $[C_{20}H_{25}FN_2O_3]^+$ 360.1849.

Example 3

Synthesis of Compound 10

(E)-2-(2-(2-(2-hydroxyethoxy)ethoxy)ethoxy)-5-(4-nitrostyryl)pyridine (7)

The mixture of potassium carbonate (158.7 mg, 1.15 mmol), compound 3 (100 mg, 0.38 mmol) and triethylene glycol (576 mg, 3.8 mmol) in anhydrous DMF (5.0 ml) was sealed in a microwavable vial (from Biotage) and subjected to microwave irradiation (Biotage Initiator system) at 180° C. for 25 min. After cooling to room temperature, water was added and reaction mixture was extracted with ethyl acetate. Organic layer was separated, washed with brine, dried over anhydrous sodium sulfate and evaporated. The residue was purified with PTLC (4% MeOH in DCM as developing solvent) gave product 7 (110 mg, Yield: 77%): $^1$H NMR (200 MHz, CDCl$_3$): δ.8.20 (3H, m), 7.83 (1H, d, d, J=8.6 Hz, J$_2$=2.4 Hz), 7.61 (2H, d, J=8.8 Hz), 7.10 (2H, m) 6.84 (1H, d, J=8.6 Hz), 4.53 (2H, t, J=4.8 Hz), 3.88 (2H, t, J=4.8 Hz), 3.71 (6H, m), 3.61 (2H, m), 2.10 (1H, b), HRMS (EI) m/z calcd. for $[C_{19}H_{22}N_2O_6]^+$ 374.1478.

(E)-2-(2-(2-(2-hydroxyethoxy)ethoxy)ethoxy)-5-(4-aminostyryl)pyridine (8)

Stannous chloride (202.8 mg, 1.07 mmol) was added to a solution of compound 7 (100 mg 0.27 mmol) in ethanol (10 ml) followed by the addition of concentrated HCl (0.5 ml). The reaction mixture was refluxed for 1.5 h and then cooled to 0° C. Yellow precipitate was collected by filtration and then suspended in ethyl acetate. Saturated NaHCO$_3$ was added to adjust pH to 9. Organic layer was separated, dried over anhydrous sodium sulfate and evaporated. The residue was purified by PTLC (5% MeOH in DCM as developing solvent) to give product 8 (70 mg, Yield: 76%): $^1$H NMR (200 MHz, CDCl$_3$): δ 8.12 (1H, d, J=2.4 Hz), 7.73 (1H, d, d, J1=8.6 Hz, J2=2.4 Hz), 7.29 (2H, d, J=8.5 Hz), 6.84 (2H, m), 6.75 (1H, d, J=8.6 Hz), 6.69 (2H, d, J=8.5 Hz), 4.48 (2H, t, J=4.8 Hz), 3.86 (2H, t, J=4.8 Hz), 3.71 (6H, m), 3.60 (2H, m), 3.32 (3H, b), HRMS (EI) m/z calcd. for $[C_{19}H_{24}N_2O_4]^+$ 344.1736.

(E)-2-(2-(2-(2-Hydroxyethoxy)ethoxy)ethoxy)-5-(4-dimethylaminostyryl)pyridine (9)

Sodium cyanoborohydride (36 mg, 0.57 mmol) was added to a solution of compound 8 (65 mg, 0.19 mmol) and paraformaldehyde (57 mg, 1.9 mmol) in acetic acid (10 ml). The reaction mixture was stirred at room temperature overnight and poured onto ice. Sodium bicarbonate was used to adjust pH to 9. Reaction mixture was extracted with ethyl acetate. Organic layer was separated, washed with brine, dried over anhydrous sodium sulfate and evaporated. The residue was purified with PTLC (5% MeOH in DCM as the developing solvent) to give product 9 (67 mg, Yield: 95%): $^1$H NMR (200 MHz, CDCl$_3$): δ.8.14 (1H, d, J=2.4 Hz), 7.76 (1H, d, d, J=8.6 Hz, J$_2$=2.4 Hz), 7.39 (2H, d, J=8.8 Hz), 6.87 (2H, m), 6.76 (3H, m), 4.50 (2H, t, J=4.8 Hz), 3.87 (2H, t, J=4.8 Hz), 3.70 (6H, m), 3.61 (2H, m), 2.98 (6H, s), 2.49 (1H, b), HRMS (EI) m/z calcd. for $[C_{21}H_{28}N_2O_4]^+$ 372.2049.

(E)-2-(2-(2-(2-tosyloxyethoxy)ethoxy)ethoxy)-5-(4-dimethylaminostyryl)pyridine (10)

Tosyl chloride (52 mg, 0.27 mmol) was added to a solution of compound 9 (43 mg, 0.116 mmol) in pyridine (5.0 ml) at 0° C. The reaction mixture was stirred at 0° C. for 1 h and then warmed up to room temperature and stirred for 3 h. Water was added and reaction mixture was extracted with ethyl acetate. Organic layer was separated, washed with brine, dried over sodium sulfate and evaporated. The residue was purified by PTLC (4% MeOH in DCM as developing solvent) to give product 10 (25 mg, Yield: 41%): $^1$H NMR (200 MHz, CDCl$_3$): δ.8.14 (1H, d, J=2.0 Hz), 7.76 (3H, m), 7.39 (2H, d, J=8.8 Hz), 7.32 (2H, d, J=8.0 Hz), 6.87 (2H, m), 6.75 (3H, m), 4.46 (2H, t, J=4.6 Hz), 4.16 (2H, t, J=4.8 Hz), 3.81 (2H, t, J=4.8 Hz), 3.66 (6H, m), 2.99 (6H, s), 2.43 (3H, s), HRMS (EI) m/z calcd. for $[C_{28}H_{34}N_2O_6S]^+$ 526.2138.

Example 4

Synthesis of Compound 11a a. Synthesis of intermediates I8 and I9

2-Hydroxy-3-bromo-5-iodopyridine (I8)

Following a previously reported method (Meana A, et al, Synlett 2003, 1678-1682) compound 18 was prepared from N-iodosuccinimide (2.48 g, 11.0 mmol) and 3-bromo-2-hydroxypyridine 17 (1.74 g, 10.0 mmol) as a pale brown solid (2.55 g, 85%). $^1$H NMR (DMSO-d$_6$) δ 12.27 (br s, 1H), 8.08 (d, 1H, J=2.3 Hz), 7.71 (d, 1H, J=2.3 Hz).

{2-[2-(2-Fluoroethoxy)ethoxy]ethoxy}-3-bromo-5-iodopyridine (I9)

To a stirring suspension of 18 (0.393 g, 1.3 mmol), 2-(2-(2-fluoroethoxy)ethoxy)ethanol (0.200 g, 1.3 mmol) and PPh$_3$ (0.511 g, 1.95 mmol) in 10 mL of THF at −10° C. was added dropwise of diisopropyl azodicarboxylate (DIAD, 0.394 g, 1.95 mmol) in 5 mL of THF. The ice-salt bath was removed and the reaction was kept at room temperature (r.t.) 2 h. The reaction solution was concentrated and purified by FC (MeOH/CHCl$_3$, 1/99) to yield 19, a colorless viscous liquid (0.423 g, 75%). $^1$H NMR δ58.21 (d, 1H, J=2.0 Hz), 8.02 (d, 1H, J=2.0 Hz), 4.66 (t, 1H, J=4.1 Hz), 4.50-4.39 (m, 3H), 3.89-3.64 (m, 8H). $^{13}$C NMR δ159.4, 151.2, 148.5, 108.5, 84.9, 81.6, 81.5, 71.1, 71.0, 70.8, 70.4, 69.3, 66.9. HRMS calcd for C$_{11}$H$_{14}$BrFINO$_3$ (M$^+$), 432.9186; found, 432.9173.

b. Synthesis of compound 11a (E)-(5-Bromo-6-{2-[2-(2-fluoroethoxy)ethoxy] ethoxy}pyridin-3-yl)-2-(4-dimethylaminophenyl)-ethylene (11a)

A mixture of 4-dimethylaminostyrene (0.110 g, 0.75 mmol), I9 (0.217 g, 0.5 mmol), K$_2$CO$_3$ (0.173 g, 1.25 mmol), tetrabutylammonium bromide (TBAB, 0.322 g, 1.0 mmol) and palladium acetate (Pd(OAc)$_2$, 0.006 g, 0.025 mmol) in 2 mL DMF was deoxygenated by purging into nitrogen for 15 min and then heated to 65° C. for 2 h. The reaction mixture was cooled to r.t. and submitted to standard workup with ethyl acetate (EtOAc). The crude product was purified by FC (EtOAc/Hexanes, 30/70) and resulted in 11a as a light yellow solid (0.178 g, 79%). $^1$H NMR δ8.08 (d, 1H, J=2.1 Hz), 8.00 (d, 1H, J=2.1 Hz), 7.39 (d, 2H, J=8.8 Hz), 6.92 (d, 1H, J=16.3

Hz), 6.74 (d, 1H, J=16.3 Hz), 6.72 (d, 2H, J=8.1 Hz), 4.69 (t, 1H, J=4.2 Hz), 4.55 (t, 2H, J=4.8 Hz), 4.45 (t, 1H, J=4.2 Hz), 3.94-3.68 (m, 8H), 3.00 (s, 6H). $^{13}$C NMR δ 158.3, 150.4, 143.5, 138.0, 129.6, 129.5, 127.7, 125.2, 118.8, 112.5, 107.5, 85.0, 81.6, 71.2, 71.0, 70.8, 70.4, 69.6, 66.7, 40.5. HRMS calcd for $C_{21}H_{26}BrFN_2O_3$ (M$^+$), 452.1111; found, 452.1099.

Example 5

Synthesis of Compound 11b (E)-(5-Bromo-6-{2-[2-(2-fluoroethoxy)ethoxy]ethoxy}pyridin-3-yl)-2-(4-methylaminophenyl)-ethylene (11b)

Compound 11b was prepared from 4-methylaminostyrene (0.073 g, 0.55 mmol) and 19 (0.217 g, 0.50 mmol) as a light yellow viscous liquid (0.113 g, 52% yield). $^1$H NMR δ8.07 (d, 1H, J=2.1 Hz), 8.00 (d, 1H, J=2.1 Hz), 7.35 (d, 2H, J=8.6 Hz), 6.91 (d, 1H, J=16.3 Hz), 6.74 (d, 1H, J=16.3 Hz), 6.60 (d, 2H, J=8.6 Hz), 4.69 (t, 1H, J=4.2 Hz), 4.55 (t, 2H, J=4.8 Hz), 4.45 (t, 1H, J=4.2 Hz), 3.94-3.68 (m, 8H), 2.88 (s, 3H). $^{13}$C NMR δ158.4, 149.5, 143.6, 138.0, 129.8, 129.5, 127.9, 126.1, 118.9, 112.6, 107.5, 85.0, 81.7, 71.2, 71.1, 70.8, 70.4, 69.6, 66.8, 30.7. HRMS calcd for $C_{20}H_{24}BrFN_2O_3$ (M$^+$), 438.0954; found, 438.0967.

Example 6

Synthesis of Compound 11e (E)-(5-Bromo-6-{2-[2-(2-fluoroethoxy)ethoxy]ethoxy}pyridin-3-yl)-2-[4-N-methyl-4-N-(tert-butyloxycarbonyl)aminophenyl]-ethylene (11c)

Compound 11c was prepared from 4-N-methyl-4-N-(tert-butyloxycarbonyl)aminostyrene (0.219 g, 0.94 mmol) and 19 (0.273 g, 0.63 mmol) as a white viscous liquid (0.319 g, 94% yield). $^1$H NMR δ8.12 (d, 1H, J=2.1 Hz), 8.03 (d, 1H, J=2.1 Hz), 7.44 (d, 2H, J=8.6 Hz), 7.25 (d, 2H, J=9.0 Hz), 6.94 (d, 2H, J=2.1 Hz), 4.69 (t, 1H, J=4.2 Hz), 4.56 (t, 2H, J=4.9 Hz), 4.45 (t, 1H, J=4.2 Hz), 3.94-3.68 (m, 8H), 3.28 (s, 3H), 1.48 (s, 9H). $^{13}$C NMR δ 158.8, 154.5, 144.0, 143.5, 138.2, 133.6, 128.5, 128.4, 126.8, 126.6, 125.4, 122.9, 107.4, 84.8, 81.4, 80.4, 71.0, 70.9, 70.6, 70.2, 69.4, 66.7, 53.5, 37.1, 28.4. HRMS calcd for $C_{25}H_{32}BrFN_2O_5$ (M$^+$), 538.1479; found, 538.1476.

(E)-(5-Bromo-6-{2-[2-(2-fluoroethoxy)ethoxy]ethoxy}pyridin-3-yl)-2-(4-acetoxyphenyl)-ethylene (11d)

Compound 11d was prepared from 4-acetoxystyrene (0.122 g, 0.75 mmol) and 19 (0.217 g, 0.5 mmol) as a white viscous liquid (0.181 g, 77% yield). $^1$H NMR δ8.12 (d, 1H, J=2.1 Hz), 8.03 (d, 1H, J=2.1 Hz), 7.50 (d, 2H, J=8.6 Hz), 7.10 (d, 2H, J=8.6 Hz), 6.94 (d, 2H, J=3.3 Hz), 4.69 (t, 1H, J=4.2 Hz), 4.56 (t, 2H, J=4.9 Hz), 4.45 (t, 1H, J=4.2 Hz), 3.94-3.68 (m, 8H), 2.32 (s, 3H), 1.48 (s, 9H). $^{13}$C NMR δ169.3, 158.9, 150.3, 144.1, 138.2, 134.5, 128.24, 128.16, 127.4, 123.4, 121.9, 107.5, 84.8, 81.5, 71.0, 70.9, 70.6, 70.3, 69.4, 66.7, 21.1. HRMS calcd for $C_{21}H_{23}BrFNO_5$ (M$^+$), 467.0744; found, 467.0731.

(E)-(5-Bromo-6-{2-[2-(2-fluoroethoxy)ethoxy]ethoxy}pyridin-3-yl)-2-(4-hydroxyphenyl)-ethylene (11e)

Acetate 11d (0.145 g, 0.31 mmol) and $K_2CO_3$ (0.064 g, 0.465 mmol) were placed in EtOH/THF (5 mL/5 mL) and the reaction mixture was stirred at r.t. 2 h. After standard workup with EtOAc, the crude product was purified by PTLC to give 11e as a white solid (0.128 g, 97%). $^1$H NMR δ8.07 (d, 1H, J=2.1 Hz), 7.99 (d, 1H, J=2.1 Hz), 7.35 (d, 2H, J=8.6 Hz), 6.96-6.74 (m, 4H), 5.22 (br s, 1H), 4.69 (t, 1H, J=4.2 Hz), 4.54 (t, 2H, J=4.8 Hz), 4.45 (t, 1H, J=4.2 Hz), 3.94-3.68 (m, 8H). $^{13}$C NMR δ158.5, 156.4, 143.6, 138.2, 129.2, 129.0, 127.9, 120.7, 116.0, 107.6, 84.9, 81.6, 71.1, 71.0, 70.8, 70.4, 69.6, 66.8. HRMS calcd for $C_{19}H_{21}BrFNO_4$ (M$^+$), 425.0638; found, 425.0651.

Example 7

Synthesis of Compound 12b (E)-(5-tri-Butylstannyl-6-{2-[2-(2-fluoroethoxy)ethoxy]ethoxy}pyridin-3-yl)-2-(4-methylaminophenyl)-ethylene (12b)

Compound 12b was prepared from 11b (0.069 g, 0.156 mmol) as a light yellow oil (0.068 g, 68% yield). $^1$H NMR δ8.10 (d, 1H, J=2.5 Hz), 7.80 (d, 1H, J=2.5 Hz), 7.36 (d, 2H, J=8.6 Hz), 6.92 (d, 1H, J=16.3 Hz), 6.80 (d, 1H, J=16.3 Hz), 6.61 (d, 2H, J=8.6 Hz), 4.69 (t, 1H, J=4.2 Hz), 4.45 (t, 3H, J=5.1 Hz), 3.83 (t, 3H, J=4.4 Hz), 3.71-3.66 (m, 5H), 2.88 (s, 3H), 1.68-1.48 (m, 6H), 1.43-1.25 (m, 6H), 1.15-1.02 (m, 6H), 0.91 (t, 9H, J=7.1 Hz). $^{13}$C NMR δ 166.8, 149.1, 145.4, 143.6, 127.8, 127.7, 127.0, 123.8, 121.2, 112.6, 85.0, 81.6, 71.1, 70.9, 70.8, 70.5, 70.1, 65.0, 30.8, 29.5, 29.3, 29.1, 28.1, 27.5, 26.9, 13.9, 13.4, 13.3, 9.9, 6.6, 6.4. HRMS calcd for $C_{32}H_{51}FN_2O_3Sn$ (M$^+$), 650.2906; found, 650.2894.

Example 8

Synthesis of Compound 12e (E)-(5-tri-Butylstannyl-6-{2-[2-(2-fluoroethoxy)ethoxy]ethoxy}pyridin-3-yl)-2-(4-hydroxyphenyl)-ethylene (12e)

Compound 12e was prepared from 11e (0.032 g, 0.075 mmol) as a white viscous liquid (0.040 g, 84% yield). $^1$H NMR δ8.11 (d, 1H, J=2.5 Hz), 7.82 (d, 1H, J=2.5 Hz), 7.39 (d, 2H, J=8.6 Hz), 6.98-6.74 (m, 4H), 5.19 (br s, 1H), 4.71-4.66 (m, 1H), 4.48-4.43 (m, 3H), 3.90-3.62 (m, 8H), 1.70-1.02 (m, 18H), 0.91 (t, 9H, J=7.1 Hz). $^{13}$C NMR δ166.9, 156.0, 145.4, 144.0, 130.1, 127.9, 127.6, 127.4, 124.3, 123.0, 115.9, 85.0, 81.6, 71.0, 70.9, 70.7, 70.5, 70.0, 65.2, 29.5, 29.3, 29.1, 28.0, 27.5, 26.9, 13.9, 13.4, 13.3, 9.9, 6.6, 6.4. HRMS calcd for $C_{31}H_{48}FNO_4Sn$ (M$^+$), 637.2589, found, 637.2573.

Example 9

Synthesis of Compound 13a (E)-(5-tri-Butylstannyl-6-{2-[2-(2-fluoroethoxy)ethoxy]ethoxy}pyridin-3-yl)-2-(4-dimethylaminophenyl)-ethylene (12a)

A mixture of 11a (0.052 g, 0.115 mmol), bis(tributyltin) ((Bu$_3$Sn)$_2$, 0.333 g, 0.57 mmol), and palladium tetrakistriphenylphosphine (Pd(PPh$_3$)$_4$, 0.013 g, 10 mol %) in toluene was heated at 110° C. for 18 h. The reaction solution was cooled to r.t. and treated with 5 mL 10% KF. After vigorously stirring for additional 0.5 h, the standard workup with EtOAc and following FC (EtOAc/Hexanes, 25/75) afforded 12a as a light yellow oil (0.052 g, 68%).

$^1$H NMR 58.11 (d, 1H, J=2.5 Hz), 7.81 (d, 1H, J=2.5 Hz), 7.41 (d, 2H, J=8.8 Hz), 6.93 (d, 1H, J=16.5 Hz), 6.81 (d, 1H, J=16.5 Hz), 6.72 (d, 2H, J=8.7 Hz), 4.69 (t, 1H, J=4.2 Hz), 4.46 (t, 3H, J=4.9 Hz), 3.83 (t, 3H, J=4.8 Hz), 3.71-3.66 (m, 5H), 3.00 (s, 6H), 1.68-1.48 (m, 6H), 1.43-1.21 (m, 6H), 1.15-1.02 (m, 6H), 0.91 (t, 9H, J=7.1 Hz). $^{13}$C NMR δ 166.7, 150.2, 145.4, 143.6, 127.8, 127.7, 127.5, 126.0, 123.7, 121.2, 112.6, 85.0, 81.6, 71.0, 70.7, 70.4, 70.0, 65.0, 40.6, 29.5, 29.3, 29.1, 28.1, 27.5, 26.9, 13.9, 13.4, 13.3, 9.9, 6.6, 6.4. HRMS calcd for $C_{33}H_{53}FN_2O_3Sn$ (M$^+$), 664.3062; found, 664.3037.

(E)-(5-Iodo-6-{2-[2-(2-fluoroethoxy)ethoxy]ethoxy}pyridin-3-yl)-2-(4-dimethylaminophenyl)-ethylene (13a)

A solution of iodine (I$_2$, 0.063 g, 0.24 mmol) in THF (2 mL) was added dropwise to an ice bath cooled solution of 12a (0.114 g, 0.172 mmol) in THF (3 mL). After the addition, the reaction was stirred at 0° C. for 1 h. Following standard workup with CH$_2$Cl$_2$, the crude product was purified by FC (EtOAc/Hexanes, 25/75) to give a light yellow solid 13a (0.037 g, 48%).

$^1$H NMR δ 8.22 (d, 1H, J=2.1 Hz), 8.10 (d, 1H, J=2.1 Hz), 7.38 (d, 2H, J=8.8 Hz), 6.92 (d, 1H, J=16.3 Hz), 6.72 (d, 1H, J=16.3 Hz), 6.71 (d, 2H, J=8.8 Hz), 4.72-4.67 (m, 1H), 4.54-4.44 (m, 3H), 3.93-3.69 (m, 8H), 3.00 (s, 6H). $^{13}$C NMR δ 160.4, 150.5, 144.6, 144.55, 129.8, 129.5, 127.8, 125.3, 118.8, 112.6, 85.1, 81.7, 80.6, 71.3, 71.1, 70.8, 70.5, 69.6, 67.1, 40.6. HRMS calcd for $C_{21}H_{26}FIN_2O_3$ (M$^+$), 500.0972; found, 500.0959.

Example 10

Synthesis of Compound 13b (E)-(5-tri-Butylstannyl-6-{2-[2-(2-fluoroethoxy)ethoxy]ethoxy}pyridin-3-yl)-2-[4-N-methyl-4-N-(tert-butyloxycarbonyl)aminophenyl]-ethylene (12c)

Compound 12c was prepared from 11c (0.072 g, 0.133 mmol) as a white viscous liquid (0.077 g, 77% yield). $^1$H NMR δ 8.14 (d, 1H, J=2.5 Hz), 7.83 (d, 1H, J=2.5 Hz), 7.46 (d, 2H, J=8.6 Hz), 7.23 (d, 2H, J=8.5 Hz), 6.96 (s, 2H), 4.70-4.66 (m, 1H), 4.49-4.42 (m, 3H), 3.86-3.66 (m, 8H), 3.28 (s, 3H), 1.80-1.02 (m, 27H), 0.90 (t, 9H, J=7.1 Hz). $^{13}$C NMR δ 167.3, 146.1, 143.8, 143.2, 134.6, 127.0, 126.8, 126.6, 125.7, 125.4, 124.1, 85.0, 81.6, 80.6, 71.1, 70.9, 70.8, 70.5, 70.0, 65.1, 37.4, 29.5, 29.3, 29.1, 28.1, 27.5, 26.9, 13.9, 13.4, 9.9, 6.4. HRMS calcd for $C_{37}H_{59}FN_2O_5Sn$ (M$^+$), 750.343; found, 750.3425.

(E)-(5-Iodo-6-{2-[2-(2-fluoroethoxy)ethoxy]ethoxy}pyridin-3-yl)-2-[4-N-methyl-4-N-(tert-butyloxycarbonyl)aminophenyl]-ethylene (13c)

Compound 13c was prepared from 12c (0.024 g, 0.032 mmol) as a white viscous liquid (0.018 g, 98%). $^1$H NMR δ 8.25 (d, 1H, J=1.6 Hz), 8.13 (d, 1H, J=1.6 Hz), 7.44 (d, 2H, J=8.4 Hz), 7.24 (d, 2H, J=8.4 Hz), 6.97 (d, 1H, J=16.4 Hz), 6.86 (d, 1H, J=16.4 Hz), 4.69 (t, 1H, J=4.1 Hz), 4.53 (t, 2H, J=4.8 Hz), 4.45 (t, 1H, J=4.1 Hz), 3.94-3.69 (m, 8H), 3.28 (s, 3H), 1.47 (s, 9H). $^{13}$C NMR δ 161.0, 154.8, 145.3, 144.9, 143.7, 133.9, 128.9, 128.6, 126.8, 125.7, 123.1, 85.1, 81.7, 80.7, 77.4, 71.3, 71.1, 70.9, 70.5, 69.6, 67.2, 37.4, 28.6. HRMS calcd for $C_{21}H_{26}FIN_2O_3$ (M$^+$), 500.0972; found, 500.0959.

(E)-(5-Iodo-6-{2-[2-(2-fluoroethoxy)ethoxy]ethoxy}pyridin-3-yl)-2-(4-methylaminophenyl)-ethylene (13b)

To a stirred solution of 13c (0.014 g, 0.024 mmol) and 2,6-lutidine (28 μL, 0.24 mmol) in 2 mL CH$_2$Cl$_2$ at 0° C. was added trimethylsilyl triflate (34 μL, 0.19 mmol). After 15 min, the reaction solution was submitted to the standard workup with CH$_2$Cl$_2$. The crude product was purified by PTLC to give a light yellow viscous liquid 13b (0.010 g, 88%). $^1$H NMR δ 8.22 (d, 1H, J=2.1 Hz), 8.10 (d, 1H, J=2.1 Hz), 7.34 (d, 2H, J=8.6 Hz), 6.91 (d, 1H, J=16.3 Hz), 6.70 (d, 1H, J=16.3 Hz), 6.60 (d, 2H, J=8.6 Hz), 4.71-4.67 (m, 1H), 4.54-4.43 (m, 3H), 3.94-3.69 (m, 9H), 2.88 (s, 3H). $^{13}$C NMR δ 160.5, 149.5, 144.6, 129.8, 129.7, 128.0, 126.3, 118.9, 112.6, 85.1, 81.7, 80.6, 77.4, 71.3, 71.2, 70.9, 70.5, 69.7, 67.2, 30.8. HRMS calcd for $C_{20}H_{24}FIN_2O_3$ (M$^+$), 486.0816; found, 486.0818.

Example 11

Synthesis of Compound 13e (E)-(5-tri-Butylstannyl-6-{2-[2-(2-fluoroethoxy)ethoxy]ethoxy}pyridin-3-yl)-2-(4-hydroxyphenyl)-ethylene (12e)

Compound 12e was prepared from 11e (0.032 g, 0.075 mmol) as a white viscous liquid (0.040 g, 84% yield). $^1$H NMR δ 8.11 (d, 1H, J=2.5 Hz), 7.82 (d, 1H, J=2.5 Hz), 7.39 (d, 2H, J=8.6 Hz), 6.98-6.74 (m, 4H), 5.19 (br s, 1H), 4.71-4.66 (m, 1H), 4.48-4.43 (m, 3H), 3.90-3.62 (m, 8H), 1.70-1.02 (m, 18H), 0.91 (t, 9H, J=7.1 Hz). $^{13}$C NMR δ 166.9, 156.0, 145.4, 144.0, 130.1, 127.9, 127.6, 127.4, 124.3, 123.0, 115.9, 85.0, 81.6, 71.0, 70.9, 70.7, 70.5, 70.0, 65.2, 29.5, 29.3, 29.1, 28.0, 27.5, 26.9, 13.9, 13.4, 13.3, 9.9, 6.6, 6.4. HRMS calcd for $C_{31}H_{48}FNO_4Sn$ (M$^+$), 637.2589; found, 637.2573.

(E)-(5-Iodo-6-{2-[2-(2-fluoroethoxy)ethoxy]ethoxy}pyridin-3-yl)-2-(4-hydroxyphenyl)-ethylene (13e)

Compound 13e was prepared from 12e (0.012 g, 0.019 mmol) as a white solid (0.008 g, 90%). $^1$H NMR δ 8.21 (d, 1H, J=2.1 Hz), 8.08 (d, 1H, J=2.1 Hz), 7.33 (d, 2H, J=8.6 Hz), 6.94-6.69 (m, 4H), 4.71-4.67 (m, 1H), 4.53-4.43 (m, 3H), 3.94-3.69 (m, 8H). HRMS calcd for $C_{19}H_{21}FINO_4$ (M$^+$), 473.0499; found, 473.0498.

Example 12

Synthesis of Compound 14a

2-Hydroxyethoxy-3-bromo-5-iodopyridine (9b)

To a stirring suspension of 18 (see Example 4 above) (0.906 g, 3.0 mmol), 2-(tert-butyl-dimethyl-silanyloxy)ethanol (0.554 g, 3.15 mmol) and PPh$_3$ (0.944 g, 3.6 mmol) in 20 mL of THF at −10° C. was added dropwise of diisopropylazodicarboxylate (DIAD) (0.728 g, 3.6 mmol) in 10 mL of THF. The ice-salt bath was removed and the reaction was kept at r.t. 2 h. The reaction solution was concentrated and purified by FC (EtOAc/Hexanes, 5/95) to afford 2-(tert-butyl-dimethyl-silanyloxy)ethoxy-3-bromo-5-iodopyridine, a colorless viscous liquid (0.995 g, 72%). $^1$H NMR δ 8.23 (d, 1H, J=2.0 Hz), 8.05 (d, 1H, J=2.0 Hz), 4.42 (t, 2H, J=4.9 Hz), 3.98 (t, 2H, J=4.9 Hz), 0.90 (s, 9H), 0.10 (s, 6H). HRMS calcd for $C_{12}H_{18}BrINO_2Si$ (M-CH$_3{}^+$), 441.9335; found, 441.9312.

(E)-[5-Bromo-6-(2-hydroxyethoxy)pyridin-3-yl]-2-(4-dimethylaminophenyl)ethylene (14a)

Compound 14a was prepared from 4-dimethylaminostyrene (0.031 g, 0.212 mmol) and 110 (0.073 g, 0.212 mmol) as a light yellow solid (0.022 g, 29% yield). $^1$H NMR δ 8.07 (d, 1H, J=2.1 Hz), 8.03 (d, 1H, J=2.1 Hz), 7.39 (d, 2H, J=8.8 Hz), 6.94 (d, 1H, J=16.3 Hz), 6.78-6.69 (m, 3H), 4.57-4.52 (m, 2H), 3.99 (t, 2H, J=4.3 Hz), 3.21 (br s, 1H), 3.00 (s, 6H). $^{13}$C NMR δ 158.3, 150.4, 143.0, 138.2, 129.9, 129.8, 127.6, 124.9, 118.3, 112.3, 107.5, 69.6, 62.1, 40.3. HRMS calcd for $C_{17}H_{19}BrN_2O_2$ (M+), 362.063; found, 362.0629.

Example 13

Synthesis of Compound 14b (E)-[5-Bromo-6-(2-hydroxyethoxy)pyridin-3-yl]-2-(4-methylaminophenyl)ethylene (14b)

Compound 14b was prepared from 4-methylaminostyrene (0.140 g, 1.05 mmol) and 110 (0.241 g, 0.7 mmol) as a light yellow viscous liquid (0.149 g, 61% yield). $^1H$ NMR δ 8.07 (d, 1H, J=2.1 Hz), 8.03 (d, 1H, J=2.1 Hz), 7.35 (d, 2H, J=8.6 Hz), 6.93 (d, 1H, J=16.3 Hz), 6.74 (d, 1H, J=16.3 Hz), 6.61 (d, 2H, J=8.6 Hz), 4.57-4.52 (m, 2H), 3.99 (br s, 2H), 3.18 (br s, 1H), 2.88 (s, 3H). $^{13}C$ NMR δ 149.6, 143.3, 138.5, 130.1, 130.0, 128.0, 126.0, 118.6, 112.6, 107.7, 69.8, 62.2, 30.7. HRMS calcd for $C_{17}H_{19}BrN_2O_2$ (M+), 348.0473; found, 348.0468.

Example 14

Synthesis of Compound 14d (E)-[5-Bromo-6-(2-hydroxyethoxy)pyridin-3-yl]-2-(4-acetoxyphenyl)ethylene (14d)

Compound 14d was prepared from 4-acetoxystyrene (0.130 g, 0.80 mmol) and 10 (0.244 g, 0.7 mmol) as a white viscous liquid (0.031 g, 12% yield). $^1H$ NMR, 8.12 (d, 1H, J=2.1 Hz), 8.08 (d, 1H, J=2.1 Hz), 7.50 (d, 2H, J=6.8 Hz), 7.11 (d, 2H, J=6.8 Hz), 6.95 (d, 2H, J=5.2 Hz), 4.58-4.54 (m, 2H), 4.01 (br s, 2H), 3.08 (br s, 1H), 2.32 (s, 3H).

Example 15

Synthesis of Compound 14e (E)-[5-Bromo-6-(2-hydroxyethoxy)pyridin-3-yl]-2-(4-hydroxyphenyl)ethylene (14e)

In a similar procedure as described in the preparation of 11e, compound 14e was prepared from Acetate 14d (0.031 g, 0.082 mmol) as a white solid (0.020 g, 73%). $^1H$ NMR (DMSO-$d_6$) δ9.60 (br s, 1H), 8.31 (s, 1H), 8.23 (s, 1H), 7.39 (d, 2H, J=8.3 Hz), 7.19 (d, 1H, J=16.8 Hz), 6.94 (d, 1H, J=16.6 Hz), 6.77 (d, 2H, J=8.3 Hz), 4.35 (t, 2H, J=5.1 Hz), 3.73 (t, 2H, J=5.1 Hz). $^{13}C$ NMR (DMSO-$d_6$)δ 157.9, 157.4, 143.7, 138.1, 129.2, 129.0, 127.8, 119.8, 115.6, 106.7, 68.4, 59.2. HRMS calcd for $C_{15}H_{14}BrNO_3$ (M+), 335.0157; found, 335.0165.

Example 16

Synthesis of Compound 15e (E)-[5-tri-Butylstannyl-6-(2-hydroxyethoxy)pyridin-3-yl]-2-(4-hydroxyphenyl)-ethylene (15e)

Compound 15e was prepared from 14e (0.031 g, 0.092 mmol) as a white viscous liquid (0.012 g, 24% yield). $^1H$ NMR δ 8.07 (d, 1H, J=2.5 Hz), 7.85 (d, 1H, J=2.5 Hz), 7.39 (d, 2H, J=8.6 Hz), 6.99-6.80 (m, 4H), 5.97 (br s, 1H), 5.01 (br s, 1H), 4.50-4.46 (m, 2H), 3.98-3.94 (m, 2H), 1.69-1.01 (m, 18H), 0.91 (t, 9H, J=7.1 Hz). 13C NMR δ 167.2, 156.0, 144.9, 144.7, 144.5, 130.1, 128.0, 127.96, 124.7, 122.8, 116.0, 69.9, 63.4, 29.9, 29.5, 29.3, 29.1, 28.1, 27.5, 26.9, 13.9, 13.6, 13.5, 10.1, 6.7, 6.6. HRMS calcd for C27H41NO3Sn (M+), 547.2108; found, 547.2112.

Example 17

Synthesis of Compound 16a (E)-[5-tri-Butylstannyl-6-(2-hydroxyethoxy)pyridin-3-yl]-2-(4-dimethylaminophenyl)-ethylene (15a)

Compound 15a was prepared from 14a (0.100 g, 0.275 mmol) as a light yellow oil (0.105 g, 66% yield). $^1H$ NMR δ 8.10 (d, 1H, J=2.5 Hz), 7.85 (d, 1H, J=2.4 Hz), 7.41 (d, 2H, J=8.7 Hz), 6.95 (d, 1H, J=16.3 Hz), 6.81 (d, 1H, J=16.6 Hz), 6.73 (d, 2H, J=8.8 Hz), 4.48-4.44 (m, 2H), 3.96-3.92 (m, 2H), 2.99 (s, 6H), 1.68-1.01 (m, 18H), 0.92 (t, 9H, J=7.2 Hz). $^{13}C$ NMR δ 166.6, 150.1, 144.5, 144.1, 128.2, 128.1, 127.4, 125.6, 124.0, 120.5, 112.4, 69.4, 63.0, 40.4, 29.0, 27.2, 13.6, 9.8. HRMS calcd for $C_{29}H_{46}N_2O_2Sn$ (M+), 574.2581; found, 574.2584.

(E)-[5-Iodo-6-(2-hydroxyethoxy)pyridin-3-yl]-2-(4-dimethylaminophenyl)ethylene (16a)

Compound 16a was prepared from 15a (0.011 g, 0.019 mmol) as a light yellow solid (0.004 g, 50%). $^1H$ NMR δ8.25 (s, 1H), 8.10 (s, 1H), 7.39 (d, 2H, J=8.6 Hz), 6.94 (d, 1H, J=16.3 Hz), 6.76-6.70 (m, 3H), 4.51 (t, 2H, J=4.2 Hz), 4.02-3.95 (m, 2H), 3.19 (s, 1H), 3.00 (s, 6H). HRMS calcd for $C_{17}H_{19}IN_2O_2$ (M+), 410.0491; found, 410.0489.

Example 18

Synthesis of Compound 16b (E)-[5-tri-Butylstannyl-6-(2-hydroxyethoxy)pyridin-3-yl]-2-(4-methylaminophenyl)-ethylene (15b)

Compound 15b was prepared from 14b (0.052 g, 0.15 mmol) as a light yellow oil (0.059 g, 64% yield). $^1H$ NMR δ8.08 (d, 1H, J=2.5 Hz), 7.84 (d, 1H, J=2.4 Hz), 7.37 (d, 2H, J=8.6 Hz), 6.93 (d, 1H, J=16.3 Hz), 6.80 (d, 1H, J=16.4 Hz), 6.61 (d, 2H, J=8.6 Hz), 4.48-4.43 (m, 2H), 3.95-3.91 (m, 2H), 2.88 (s, 3H), 1.69-1.01 (m, 18H), 0.91 (t, 9H, J=7.1 Hz). $^{13}C$ NMR δ 166.9, 149.2, 144.7, 144.3, 128.4, 128.3, 127.8, 126.7, 124.2, 120.7, 112.6, 69.6, 63.2, 30.8, 29.5, 29.3, 29.1, 28.0, 27.5, 26.9, 13.9, 13.5, 13.4, 10.0, 6.6, 6.5. HRMS calcd for $C_{28}H_{44}N_2O_2Sn$ (M+), 560.2425; found, 560.2419.

(E)-[5-Iodo-6-(2-hydroxyethoxy)pyridin-3-yl]-2-(4-methylaminophenyl)ethylene (16b)

Compound 16b was prepared from 15b (0.032 g, 0.057 mmol) as a light yellow solid (0.005 g, 21%). $^1H$ NMR δ8.24 (d, 1H, J=2.1 Hz), 8.09 (d, 1H, J=2.0 Hz), 7.36 (d, 2H, J=8.5 Hz), 6.92 (d, 1H, J=16.3 Hz), 6.76-6.64 (m, 3H), 4.53-4.49 (m, 2H), 4.01-3.96 (m, 2H), 2.96 (s, 1H), 2.89 (s, 3H). HRMS calcd for $C_{16}H_{17}IN_2O_2$ (M+), 396.0335; found, 396.0335.

Example 19

Radioiodination

Radioiodinated compounds, [$^{125}I$]13a, 13b, 16a, 16b and 16e, were prepared via iododestannylation reactions from the corresponding tributyltin precursors according to the method described previously (ref). Hydrogen peroxide (50 μL, 3% w/v) was added to a mixture of 50 μL of the tributyltin precursor (4 μg/μL EtOH), 50 μL of 1N HCl and [$^{125}I$]NaI (1-5 mCi purchased from Perkin Elmer) in a sealed vial. The reaction was allowed to proceed for 5-10 min at room temperature and terminated by addition of 100 μL of sat.

NaHSO₃. The reaction mixture was extracted with ethyl acetate (3×1 mL) after neutralization with 1.5 mL of saturated sodium bicarbonate solution. The combined extracts were evaporated to dryness. The residues were dissolved in 100 µL of EtOH and purified by HPLC using a reversed-phase column (Phenomenex Gemini C18 analytical column, 4.6×250 mm, 5 µm, CH₃CN/Ammonium formate buffer (1 mM) 8/2 or 7/3; flow rate 0.5-1.0 mL/min). The no-carrier-added products were evaporated to dryness and re-dissolved in 100% EtOH (1 µCi/µL) to be stored at −20° C. up to 6 weeks for animal studies and autoradiography studies.

Example 20

Binding Studies

Figure 6:
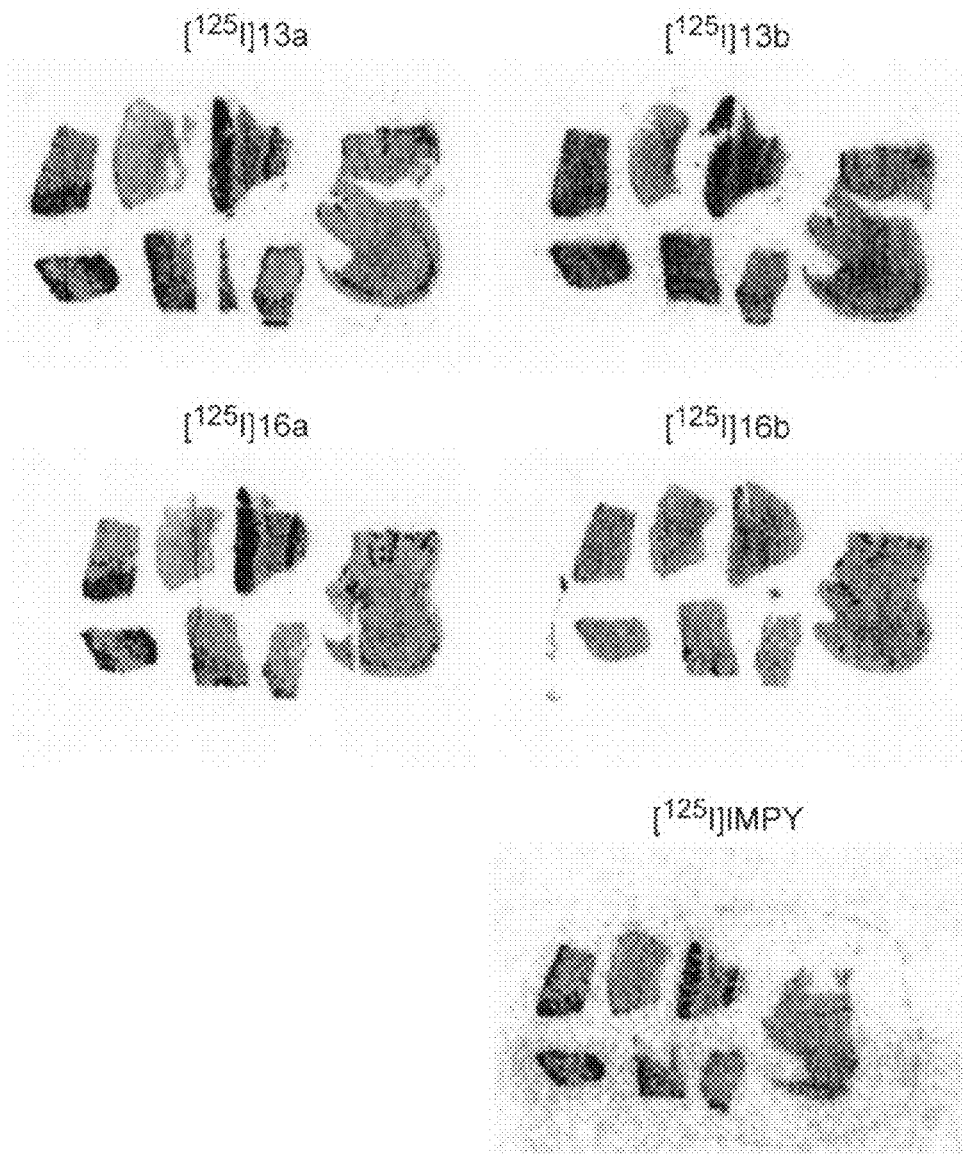
FIG. 6 depicts in vitro autoradiography of macroarray brain sections.
Figure 7:
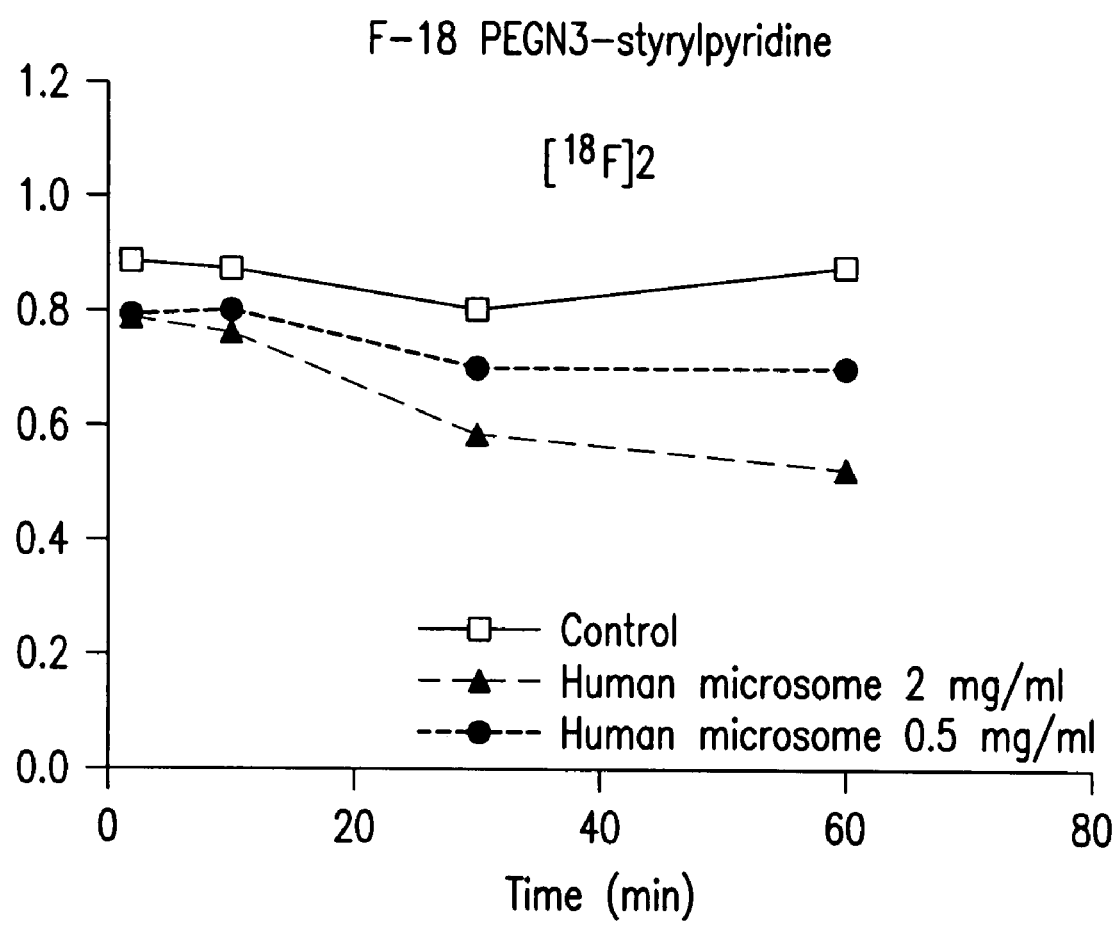
FIG. 7 depicts the in vitro stability of F-18 labeled tracers toward pooled human liver microsomal fractions. Tracers in PBS without microsomal fractions served as the control. Values (% of unchanged parent compound) were average of duplicates.
Figure 8:
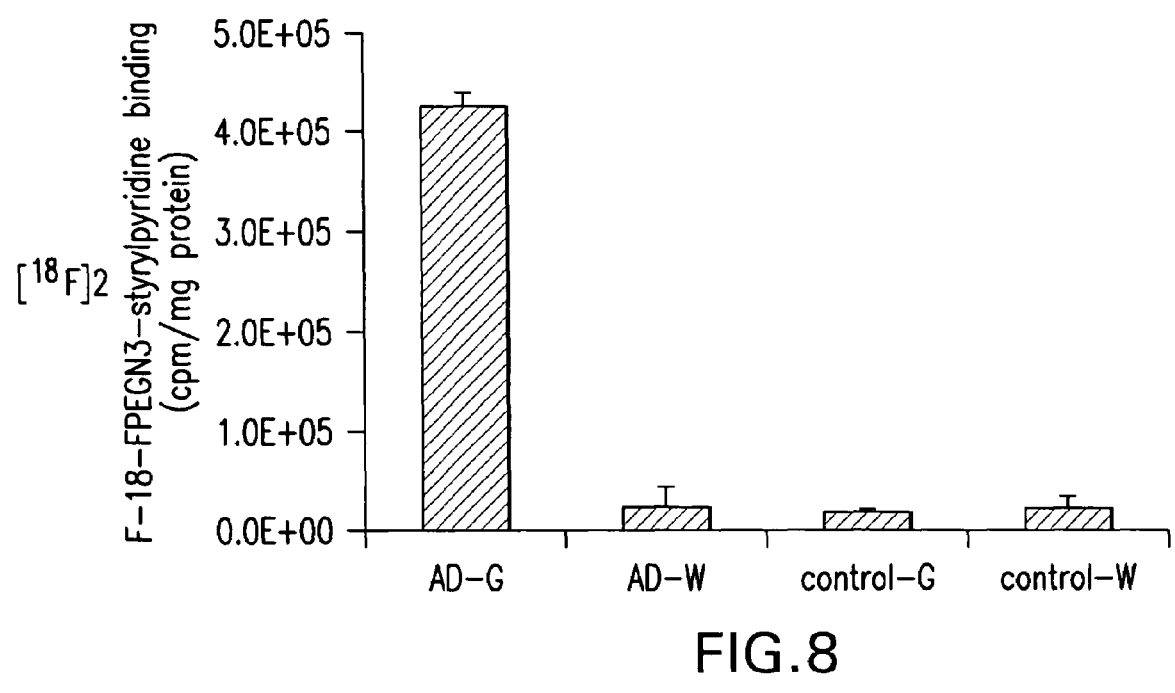
FIG. 8 depicts specific binding of [$^{18}$F]2 to pooled AD and control brain tissue homogenates. Gray and white matters were dissected from the cortical regions. High specific binding was detected mainly in gray matter. The values presented are the mean ±SEM of six measurements. Relatively low binding was observed in white matter homogenates. In contrast, homogenates of control brain, either grey or white matters, showed significantly lower specific binding of [$^{18}$F]2.
Figure 9:
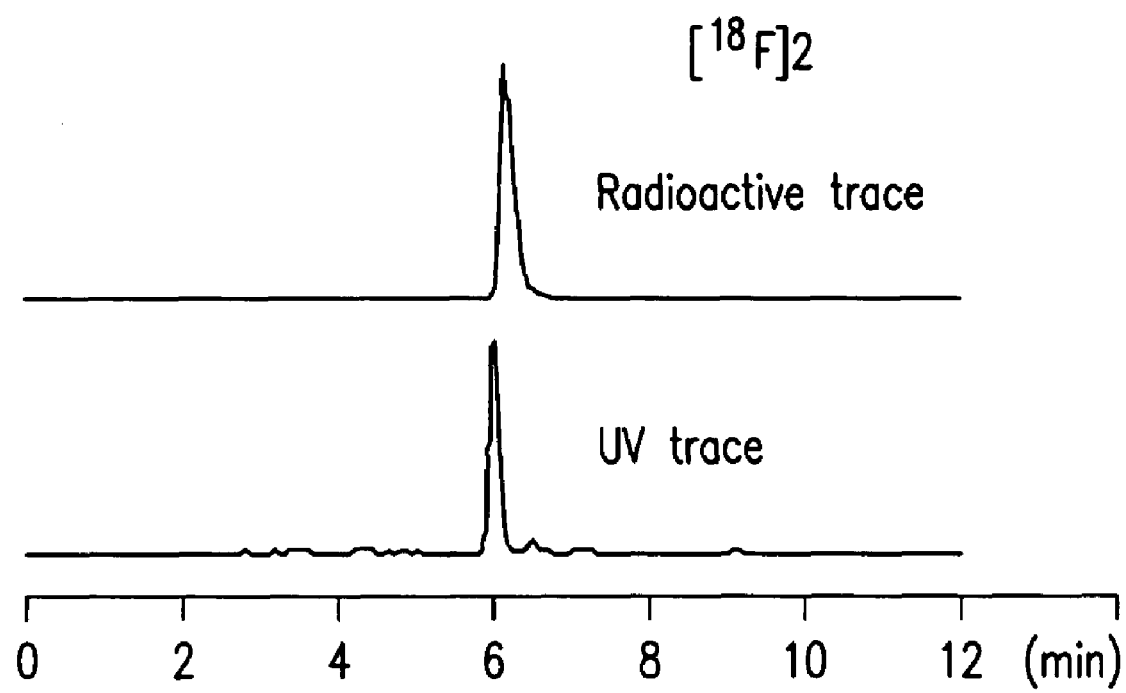
FIG. 9 depicts: (top) HPLC profile of compound [$^{18}$F]2; (bottom) UV trace of non-radioactive reference compound 2, (350 nm). HPLC condition: Agilent 1100 series; Phenomenex Gemini C-18 column 5μ 250×4.6 mm, CH$_3$CN/Ammonium formate buffer (1 mM) 8/2 v/v, 1 mL/min. Rt. 6.34 min (radioactive), 6.05 min (UV). Retention time gap was due to the detector configuration.
Figure 3:
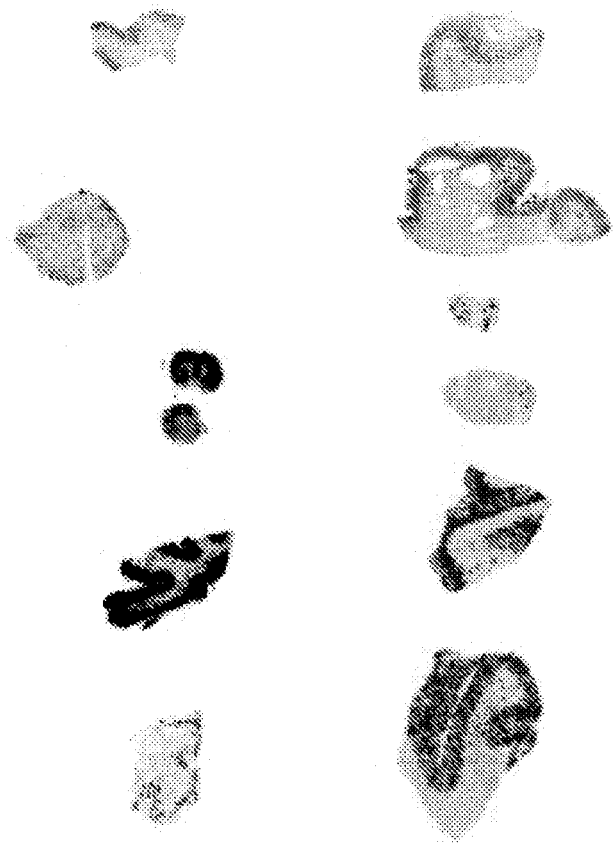
Figure 4:
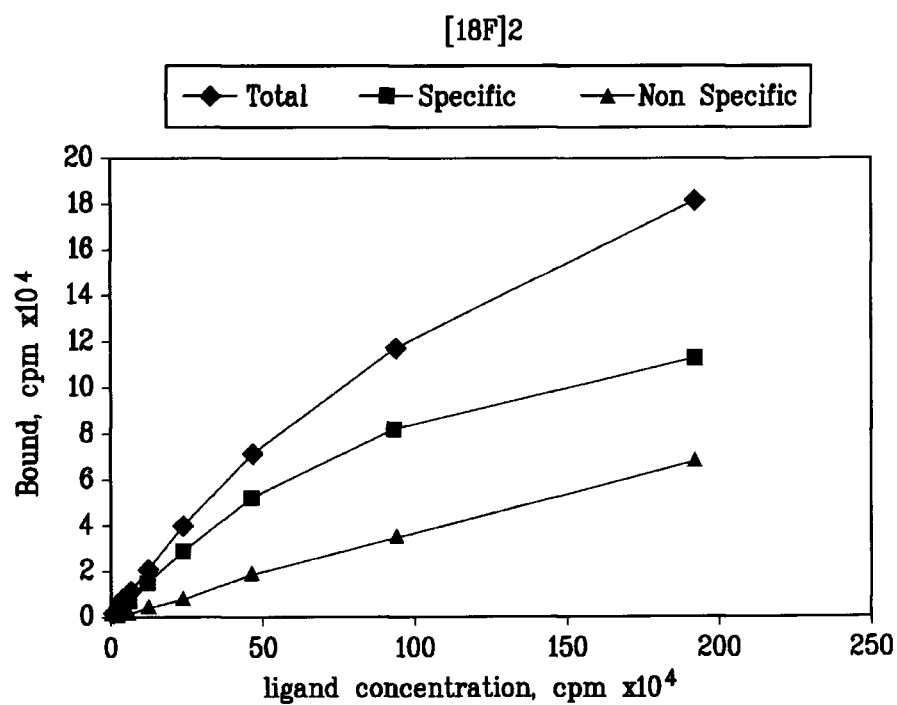
Figure 4:
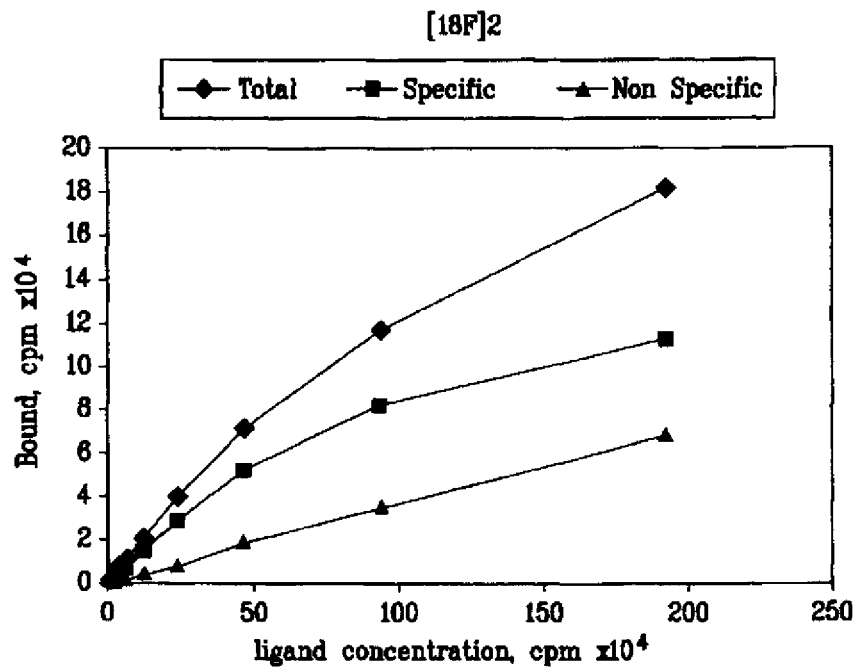

[$^{125}$I]IMPY with 2,200 Ci/mmol specific activity and greater than 95% radiochemical purity was prepared using the standard iododestannylation reaction, and purified by a simplified C-4 mini-column as described previously in Kung, M.-P.; Hou, C.; Zhuang, Z.-P.; Cross, A. J.; Maier, D. L.; Kung, H. F., "Characterization of IMPY as a potential imaging agent for b-amyloid plaques in double transgenic PSAPP mice." Eur. J. Nucl. Med. Mol. Imaging 2004, 31, 1136-1145. Competition binding assays were carried out in 12×75 mm borosilicate glass tubes. The reaction mixture contained 50 µl of pooled AD brain homogenates (20-50 µg), 50 µl of [$^{125}$I] IMPY (0.04-0.06 nM diluted in PBS) and 50 µl of inhibitors (10$^{-5}$-10$^{-10}$ M diluted serially in PBS containing 0.1% bovine serum albumin) in a final volume of 1 ml. Nonspecific binding was defined in the presence of 600 nM IMPY in the same assay tubes. The mixture was incubated at 37° C. for 2 h and the bound and the free radioactivity were separated by vacuum filtration through Whatman GF/B filters using a Brandel M-24R cell harvester followed by 2×3 ml washes of PBS at room temperature. Filters containing the bound I-125 ligand were counted in a gamma counter (Packard 5000) with 70% counting efficiency. Under the assay conditions, the specifically bound fraction was less than 15% of the total radioactivity. The results of inhibition experiments were subjected to nonlinear regression analysis using equilibrium binding data analysis from which $K_i$ values were calculated. FIGS. 1 and 6 show $K_i$ values for selected compounds of the present invention.

Example 21

Film Autoradiography

[$^{18}$F]tracers: Brain sections from AD subjects were obtained by freezing the brain in powdered dry ice and cut into 20 micrometer-thick sections. The sections were incubated with [$^{18}$F]tracers (200,000-250,000 cpm/200 µl) for 1 hr at room temperature. The sections were then dipped in saturated Li₂CO3 in 40% EtOH (two two-minute washes) and washed with 40% EtOH (one two-minute wash) followed by rinsing with water for 30 sec. After drying, the $^{18}$F-labeled sections were exposed to Kodak MR film overnight. The results are depicted in the film in FIG. 2.

[$^{125}$I]tracers: To compare different probes using similar sections of human brain tissue, human macro-array brain sections from 6 confirmed AD cases and one control subject were assembled. The presence and localization of plaques on the sections was confirmed with immunohistochemical staining with monoclonal Aβ antibody 4G8 (Sigma). The sections were incubated with [$^{125}$I]tracers (200,000-250,000 cpm/200 µL) for 1 h at room temperature. The sections were then dipped in saturated Li₂CO₃ in 40% EtOH (two two-minute washes) and washed with 40% EtOH (one two-minute wash) followed by rinsing with water for 30 sec. After drying, the $^{125}$I-labeled sections were exposed to Kodak Biomax MR film overnight.

Example 22

Organ Distribution in Mice

While under isoflurane anesthesia, 0.15 mL of a 0.1% bovine serum albumin solution containing [$^{125}$I]tracers (5-10 µCi) was injected directly into the tail vein of ICR mice (22-25 g, male). The mice (n=3 for each time point) were sacrificed by cervical dislocation at designated time-points post injection. The organs of interest were removed and weighed, and the radioactivity was counted with an automatic gamma counter. The percentage dose per organ was calculated by a comparison of the tissue counts to suitably diluted aliquots of the injected material. The total activity of the blood was calculated under the assumption that it is 7% of the total body weight. The % dose/g of samples was calculated by comparing the sample counts with the count of the diluted initial dose.

TABLE 1

Biodistribution in ICR mice after iv injection of [$^{18}$F]10 in 5% EtOH in saline (% dose/g, avg of 3 mice ± SD)

| Organ | 2 min | 30 min | 1 hr | 2 hr |
|---|---|---|---|---|
| Blood | 6.05 ± 0.33 | 2.65 ± 0.22 | 3.48 ± 0.47 | 2.15 ± 0.25 |
| Heart | 0.75 ± 0.14 | 0.17 ± 0.03 | 0.22 ± 0.03 | 0.18 ± 0.08 |
| Muscle | 7.03 ± 1.30 | 8.58 ± 0.26 | 10.62 ± 2.59 | 5.96 ± 0.06 |
| Lung | 1.07 ± 0.20 | 0.30 ± 0.01 | 0.35 ± 0.07 | 0.20 ± 0.36 |
| Kidney | 6.38 ± 0.95 | 1.68 ± 0.11 | 1.96 ± 0.21 | 0.96 ± 1.58 |
| Spleen | 0.43 ± 0.11 | 0.15 ± 0.05 | 0.13 ± 0.03 | 0.10 ± 0.17 |
| Liver | 24.90 ± 1.49 | 9.26 ± 0.83 | 10.52 ± 2.18 | 6.86 ± 0.59 |
| Skin | 2.52 ± 0.24 | 3.99 ± 0.34 | 4.42 ± 0.65 | 2.91 ± 0.16 |
| Brain | 3.49 ± 0.58 | 0.48 ± 0.07 | 0.55 ± 0.10 | 0.37 ± 0.08 |
| Bone | 5.97 ± 0.56 | 2.52 ± 0.34 | 4.39 ± 0.40 | 6.49 ± 0.08 |
| Blood | 3.04 ± 0.29 | 1.33 ± 0.16 | 1.80 ± 0.16 | 1.08 ± 0.06 |
| Heart | 6.00 ± 1056 | 1.28 ± 0.16 | 1.66 ± 0.24 | 1.32 ± 0.33 |
| Muscle | 0.62 ± 0.10 | 0.75 ± 0.04 | 0.95 ± 0.18 | 0.52 ± 0.08 |
| Lung | 5.65 ± 0.89 | 1.73 ± 0.17 | 1.82 ± 0.31 | 0.98 ± 0.08 |
| Kidney | 14.19 ± 2.34 | 3.77 ± 0.36 | 4.29 ± 0.52 | 2.19 ± 0.36 |
| Spleen | 4.65 ± 0.76 | 1.57 ± 0.51 | 1.56 ± 0.17 | 1.14 ± 0.18 |
| Liver | 17.00 ± 0.69 | 7.21 ± 0.69 | 8.13 ± 1.42 | 4.96 ± 0.90 |
| Skin | 0.59 ± 0.03 | 0.93 ± 0.13 | 1.06 ± 0.09 | 0.68 ± 0.16 |
| Brain | 7.77 ± 1.34 | 1.03 ± 0.11 | 1.28 ± 0.20 | 0.84 ± 0.08 |
| Bone | 1.49 ± 0.08 | 0.63 ± 0.12 | 1.13 ± 0.01 | 1.64 ± 0.50 |

TABLE 2

Biodistribution in ICR mice after iv injections of [$^{125}$I]-labeled tracers
(% dose/g, avg of 3 mice ± SD)

[$^{125}$I]13a (logP = 2.59)

| Organ | 2 min | 30 min | 1 hr | 2 hr |
|---|---|---|---|---|
| Blood | 2.70 ± 0.58 | 2.05 ± 0.18 | 1.65 ± 0.45 | 1.45 ± 0.41 |
| Heart | 12.76 ± 1.24 | 1.63 ± 0.03 | 0.97 ± 0.16 | 0.73 ± 0.17 |
| Muscle | 0.90 ± 0.20 | 1.00 ± 0.08 | 0.59 ± 0.13 | 0.53 ± 0.08 |
| Lung | 10.08 ± 2.15 | 2.50 ± 0.14 | 1.62 ± 0.46 | 1.33 ± 0.39 |
| Kidney | 16.62 ± 1.96 | 3.32 ± 0.11 | 2.30 ± 0.54 | 1.71 ± 0.24 |
| Spleen | 4.47 ± 1.28 | 1.42 ± 0.05 | 0.99 ± 0.47 | 0.79 ± 0.27 |
| Liver | 22.15 ± 4.34 | 9.54 ± 1.30 | 5.34 ± 2.22 | 5.62 ± 1.31 |
| Skin | 0.54 ± 0.05 | 1.47 ± 0.26 | 1.59 ± 0.68 | 1.23 ± 0.41 |
| Brain | 4.03 ± 0.43 | 1.93 ± 0.18 | 0.68 ± 0.17 | 0.26 ± 0.04 |
| Thyroid | 3.89 ± 0.67 | 16.23 ± 11.75 | 24.19 ± 8.26 | 60.76 ± 6.09 |

[$^{125}$I]13b (log P = 2.54)

| Organ | 2 min | 30 min+ | 1 hr | 2 hr |
|---|---|---|---|---|
| Blood | 4.37 ± 1.07 | 3.83 ± 1.11 | 2.88 ± 0.28 | 2.21 ± 0.73 |
| Heart | 9.85 ± 1.78 | 2.54 ± 0.37 | 1.75 ± 0.26 | 1.22 ± 0.28 |
| Muscle | 1.04 ± 0.25 | 1.11 ± 0.34 | 0.85 ± 0.06 | 0.44 ± 0.19 |
| Lung | 6.85 ± 0.27 | 3.01 ± 0.96 | 2.37 ± 0.29 | 1.85 ± 0.74 |
| Kidney | 9.03 ± 6.81 | 3.40 ± 0.76 | 2.81 ± 0.70 | 1.86 ± 0.36 |
| Spleen | 4.41 ± 1.05 | 2.49 ± 0.75 | 1.75 ± 0.33 | 1.27 ± 0.24 |
| Liver | 26.24 ± 4.47 | 11.47 ± 2.10 | 7.70 ± 1.22 | 6.25 ± 1.79 |
| Skin | 1.48 ± 0.07 | 2.95 ± 0.81 | 2.46 ± 0.16 | 1.32 ± 0.41 |
| Brain | 6.22 ± 1.01 | 1.23 ± 0.13 | 0.62 ± 0.17 | 0.26 ± 0.01 |
| Thyroid | 5.74 ± 0.42 | 24.09 ± 27.44 | 38.09 ± 6.37 | 215.05 ± 74.59 |

[$^{125}$I]16a (log P = 2.64)

| Organ | 2 min | 30 min | 1 hr+ | 2 hr |
|---|---|---|---|---|
| Blood | 2.71 ± 0.07 | 2.24 ± 0.38 | 2.18 ± 0.66 | 1.01 ± 0.02 |
| Heart | 10.24 ± 0.45 | 1.93 ± 0.27 | 1.12 ± 0.02 | 0.62 ± 0.12 |
| Muscle | 0.71 ± 0.46 | 1.05 ± 0.20 | 0.55 ± 0.03 | 0.22 ± 0.04 |
| Lung | 9.41 ± 0.56 | 3.02 ± 0.38 | 1.98 ± 0.21 | 1.00 ± 0.15 |
| Kidney | 14.25 ± 1.98 | 4.19 ± 0.45 | 2.49 ± 0.33 | 1.48 ± 0.20 |
| Spleen | 4.40 ± 1.89 | 1.94 ± 0.19 | 1.32 ± 0.10 | 0.80 ± 0.11 |
| Liver | 19.12 ± 2.68 | 12.38 ± 1.29 | 6.22 ± 0.96 | 4.87 ± 0.46 |
| Skin | 0.46 ± 0.13 | 1.18 ± 0.26 | 1.16 ± 0.00 | 0.40 ± 0.05 |
| Brain | 5.43 ± 0.85 | 3.56 ± 0.32 | 1.32 ± 0.00 | 0.46 ± 0.05 |
| Thyroid | 4.15 ± 0.43 | 11.21 ± 7.88 | 59.13 ± 6.26 | 24.81 ± 0.62 |

| Organ | 2 min | 30 min | 1 hr | 2 hr |
|---|---|---|---|---|

[$^{125}$I]16b (log P = 2.20)

| Organ | 2 min | 30 min | 1 hr | 2 hr |
|---|---|---|---|---|
| Blood | 4.14 ± 0.41 | 3.08 ± 0.35 | 1.81 ± 0.56 | 1.96 ± 0.14 |
| Heart | 7.16 ± 1.16 | 1.50 ± 0.18 | 0.88 ± 0.30 | 0.76 ± 0.03 |
| Muscle | 1.15 ± 0.38 | 0.91 ± 0.06 | 0.42 ± 0.08 | 0.38 ± 0.02 |
| Lung | 7.43 ± 1.21 | 2.67 ± 0.46 | 1.76 ± 0.32 | 1.58 ± 0.10 |
| Kidney | 11.51 ± 1.48 | 3.73 ± 0.75 | 2.16 ± 0.08 | 1.53 ± 0.20 |
| Spleen | 4.08 ± 0.68 | 1.34 ± 0.29 | 0.87 ± 0.37 | 1.08 ± 0.15 |
| Liver | 20.84 ± 2.38 | 12.57 ± 3.03 | 5.62 ± 0.68 | 3.41 ± 0.20 |
| Skin | 0.95 ± 0.09 | 1.86 ± 0.50 | 1.29 ± 0.51 | 1.43 ± 0.10 |
| Brain | 8.04 ± 0.82 | 0.88 ± 0.30 | 0.26 ± 0.03 | 0.15 ± 0.02 |
| Thyroid | 6.31 ± 1.59 | 17.23 ± 14.23 | 36.69 ± 37.17 | 99.88 ± 69.45 |

[$^{125}$I]16e (log P = 1.98)

| Organ | 2 min | 30 min | 1 hr | 2 hr |
|---|---|---|---|---|
| Blood | 10.09 ± 1.12 | 3.92 ± 0.07 | 1.29 ± 0.05 | 1.56 ± 0.04 |
| Heart | 6.66 ± 0.31 | 1.35 ± 0.16 | 0.65 ± 0.21 | 0.51 ± 0.09 |
| Muscle | 1.01 ± 0.34 | 0.59 ± 0.05 | 0.21 ± 0.02 | 0.12 ± 0.01 |
| Lung | 14.22 ± 0.92 | 3.10 ± 0.05 | 1.34 ± 0.11 | 1.02 ± 0.01 |
| Kidney | 20.40 ± 2.20 | 10.03 ± 2.12 | 2.94 ± 0.17 | 2.50 ± 1.32 |
| Spleen | 4.20 ± 0.31 | 1.28 ± 0.44 | 0.50 ± 0.03 | 0.50 ± 0.06 |
| Liver | 18.27 ± 1.29 | 5.15 ± 0.61 | 2.38 ± 0.58 | 2.63 ± 1.30 |
| Skin | 0.64 ± 0.20 | 1.36 ± 0.07 | 0.62 ± 0.01 | 0.37 ± 0.08 |
| Brain | 0.99 ± 0.24 | 0.26 ± 0.03 | 0.09 ± 0.01 | 0.06 ± 0.01 |
| Thyroid | 4.38 ± 0.46 | 3.99 ± 3.56 | 13.02 ± 8.11 | 16.02 ± 11.52 |

It will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A compound having the formula:

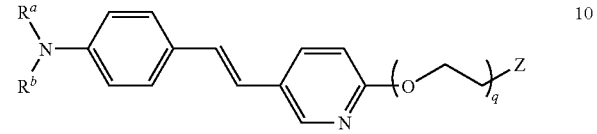

wherein, $R^a$ and $R^b$ are independently hydrogen or $C_{1-4}$alkyl; Z is I, $^{123}$I, $^{125}$I, $^{131}$I, Br, $^{76}$Br, $^{77}$Br, F, $^{18}$F, or —OTosyl; and q is an integer from 2 to 5.

2. The compound of claim 1, wherein q is 3 or 4.

3. The compound of claim 1, wherein $R^a$ is methyl and $R^b$ is hydrogen.

4. The compound of claim 1 having the formula:

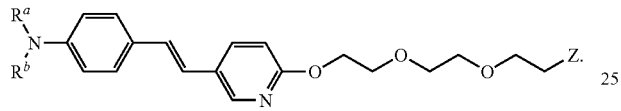

5. The compound of claim 4 having the formula:

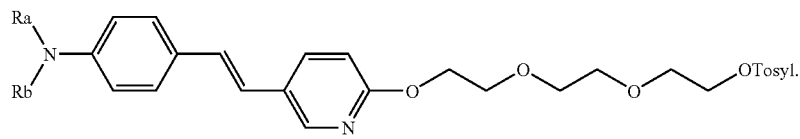

6. The compound of claim 5 having the formula:

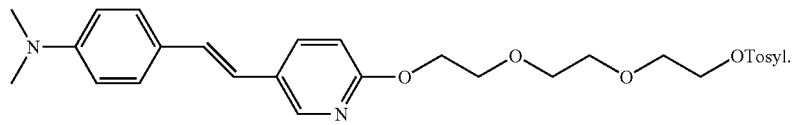

7. The compound of claim 1 having the formula:

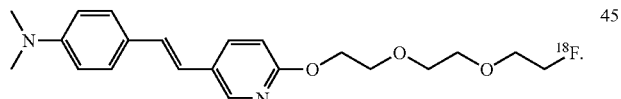

8. The compound of claim 1 having the formula:

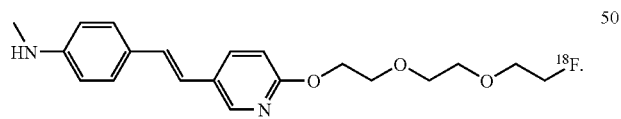

9. The compound of claim 1, wherein $R^a$ and $R^b$ are independently hydrogen or methyl and q is an integer equal to 5.

10. A diagnostic composition for imaging amyloid deposits, comprising a radiolabeled compound of claim 1.

11. A method of imaging amyloid deposits in a mammal, comprising:
    introducing into the mammal a detectable quantity of a diagnostic composition of claim 10;
    allowing sufficient time for the labeled compound to be associated with amyloid deposits; and
    detecting the labeling compound associated with one or more amyloid deposits.

* * * * *

UNITED STATES PATENT AND TRADEMARK OFFICE
CERTIFICATE OF CORRECTION

PATENT NO. : 7,687,052 B2
APPLICATION NO. : 11/727401
DATED : March 30, 2010
INVENTOR(S) : Hank F. Kung et al.

Page 1 of 4

It is certified that error appears in the above-identified patent and that said Letters Patent is hereby corrected as shown below:

In the Drawings:
Delete Figure 1 and replace with the following:

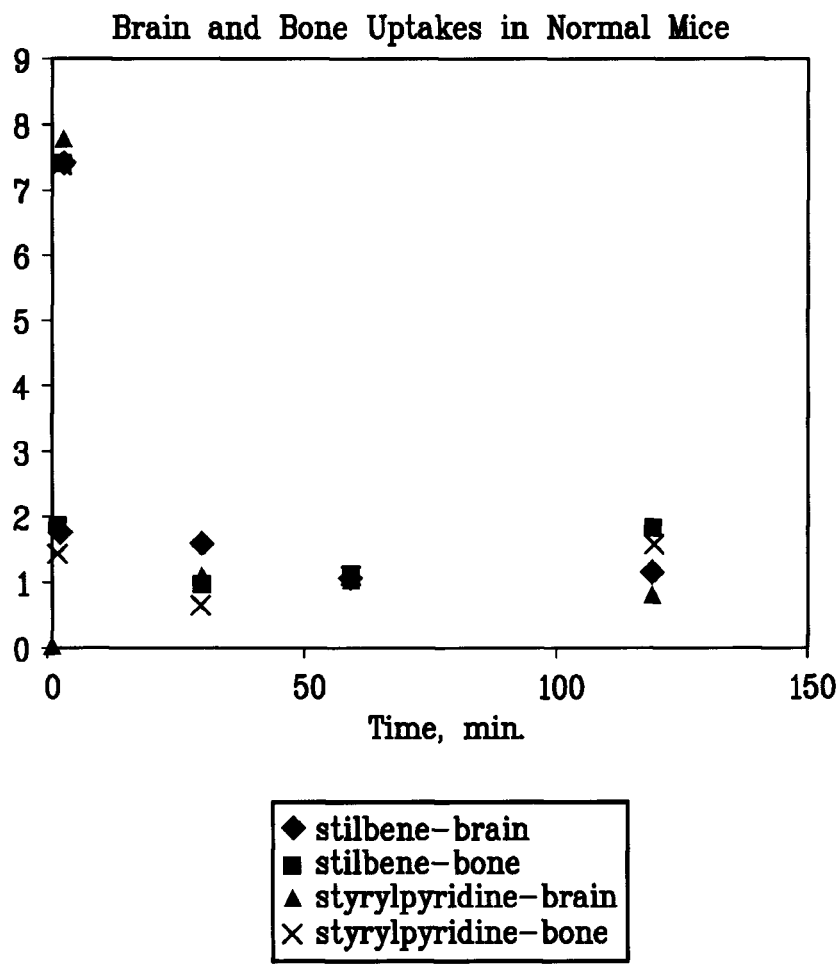

Signed and Sealed this
Fourth Day of October, 2011

David J. Kappos
*Director of the United States Patent and Trademark Office*

Figure 2:
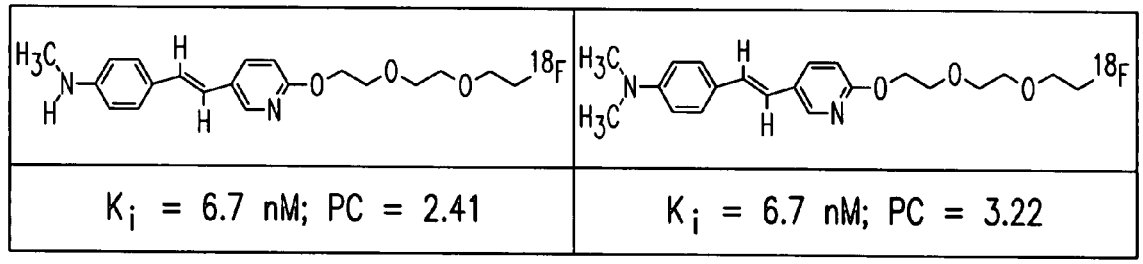
FIG. 2 depicts brain and bone uptake of styrylpyridine 2 in comparison to a stilbene analog.
Figure 2:
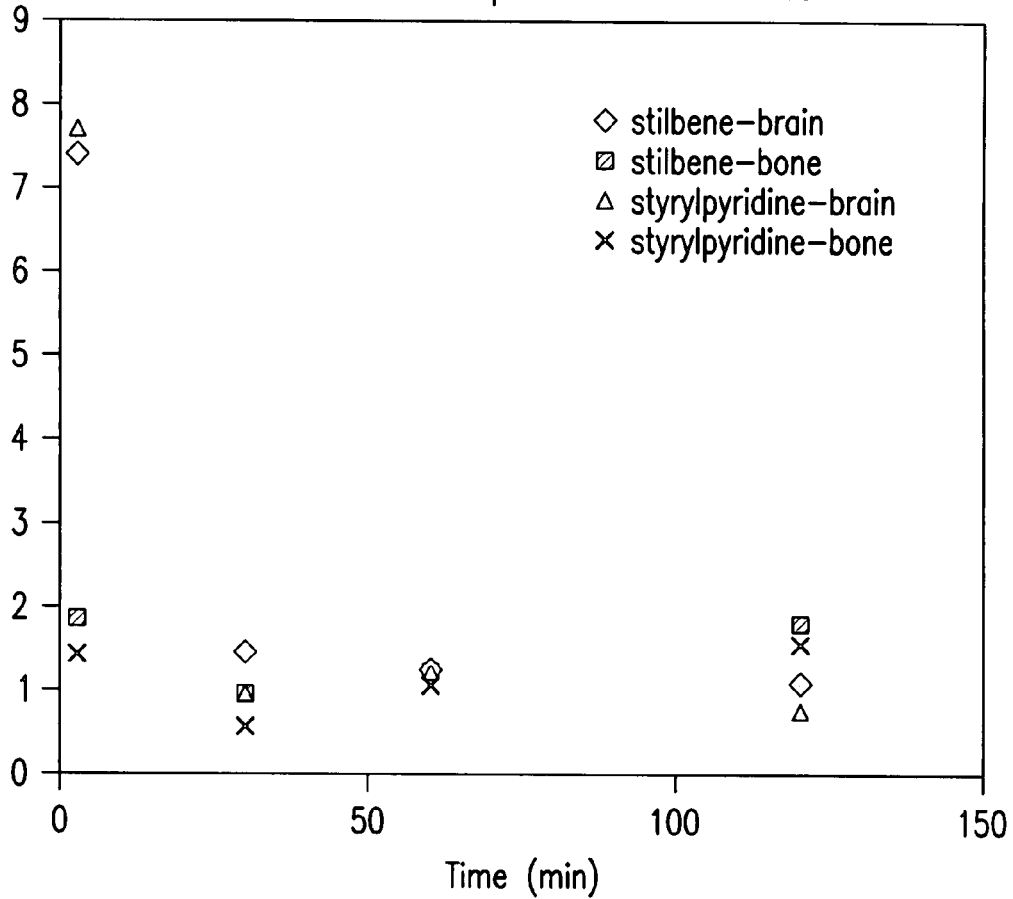

Delete Figure 2 and replace with the following:

Delete Figure 2 and replace with the following:

Column 40, lines 38-65, delete Table 1 and replace with the following:

Table 1. Biodistribution in ICR mice after iv injection of $[^{18}F]2$ in 5% EtOH in saline (%dose/g, avg of 3 mice ± SD)

| Organ | 2 min | 30 min | 1 hr | 2 hr |
|---|---|---|---|---|
| Blood | 6.05 ±0.33 | 2.65 ±0.22 | 3.48 ±0.47 | 2.15 ±0.25 |
| Heart | 0.75 ±0.14 | 0.17 ±0.03 | 0.22 ±0.03 | 0.18 ±0.08 |
| Muscle | 7.03 ±1.30 | 8.58 ±0.26 | 10.62 ±2.59 | 5.96 ±0.06 |
| Lung | 1.07 ±0.20 | 0.30 ±0.01 | 0.35 ±0.07 | 0.20 ±0.36 |
| Kidney | 6.38 ±0.95 | 1.68 ±0.11 | 1.96 ±0.21 | 0.96 ±1.58 |
| Spleen | 0.43 ±0.11 | 0.15 ±0.05 | 0.13 ±0.03 | 0.10 ±0.17 |
| Liver | 24.90 ±1.49 | 9.26 ±0.83 | 10.52 ±2.18 | 6.86 ±0.59 |
| Skin | 2.52 ±0.24 | 3.99 ±0.34 | 4.42 ±0.65 | 2.91 ±0.16 |
| Brain | 3.49 ±0.58 | 0.48 ±0.07 | 0.55 ±0.10 | 0.37 ±0.08 |
| Bone | 5.97 ±0.56 | 2.52 ±0.34 | 4.39 ±0.40 | 6.49 ±0.08 |

| Organ | 2 min | 30 min | 1 hr | 2 hr |
|---|---|---|---|---|
| Blood | 3.04 ±0.29 | 1.33 ±0.16 | 1.80 ±0.16 | 1.08 ±0.06 |
| Heart | 6.00 ±1056 | 1.28 ±0.16 | 1.66 ±0.24 | 1.32 ±0.33 |
| Muscle | 0.62 ±0.10 | 0.75 ±0.04 | 0.95 ±0.18 | 0.52 ±0.08 |
| Lung | 5.65 ±0.89 | 1.73 ±0.17 | 1.82 ±0.31 | 0.98 ±0.08 |
| Kidney | 14.19 ±2.34 | 3.77 ±0.36 | 4.29 ±0.52 | 2.19 ±0.36 |
| Spleen | 4.65 ±0.76 | 1.57 ±0.51 | 1.56 ±0.17 | 1.14 ±0.18 |
| Liver | 17.00 ±0.69 | 7.21 ±0.69 | 8.13 ±1.42 | 4.96 ±0.90 |
| Skin | 0.59 ±0.03 | 0.93 ±0.13 | 1.06 ±0.09 | 0.68 ±0.16 |
| Brain | 7.77 ±1.34 | 1.03 ±0.11 | 1.28 ±0.20 | 0.84 ±0.08 |
| Bone | 1.49 ±0.08 | 0.63 ±0.12 | 1.13 ±0.01 | 1.64 ±0.50 |

UNITED STATES PATENT AND TRADEMARK OFFICE
CERTIFICATE OF CORRECTION

PATENT NO. : 7,687,052 B2  
APPLICATION NO. : 11/727401  
DATED : March 30, 2010  
INVENTOR(S) : Hank F. Kung et al.

Page 1 of 4

It is certified that error appears in the above-identified patent and that said Letters Patent is hereby corrected as shown below:

In the Drawings:
Delete Figure 2 and replace with the following:

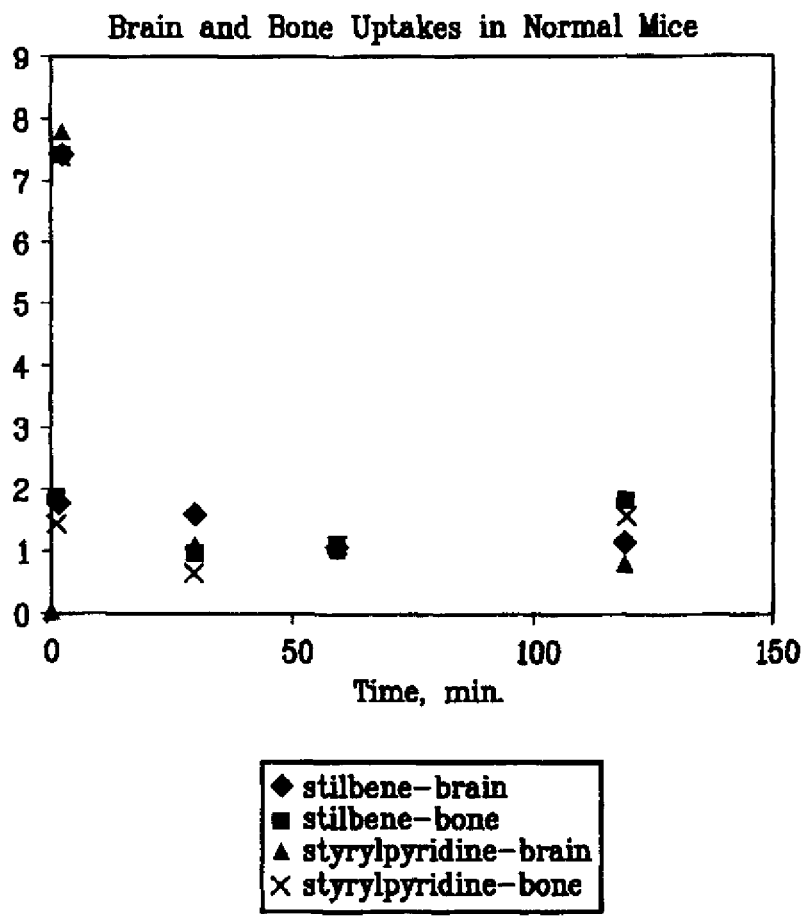

This certificate supersedes the Certificate of Correction issued October 4, 2011.

Signed and Sealed this  
Twenty-fifth Day of October, 2011

David J. Kappos  
*Director of the United States Patent and Trademark Office*

CERTIFICATE OF CORRECTION (continued)
U.S. Pat. No. 7,687,052 B2

Figure 3:
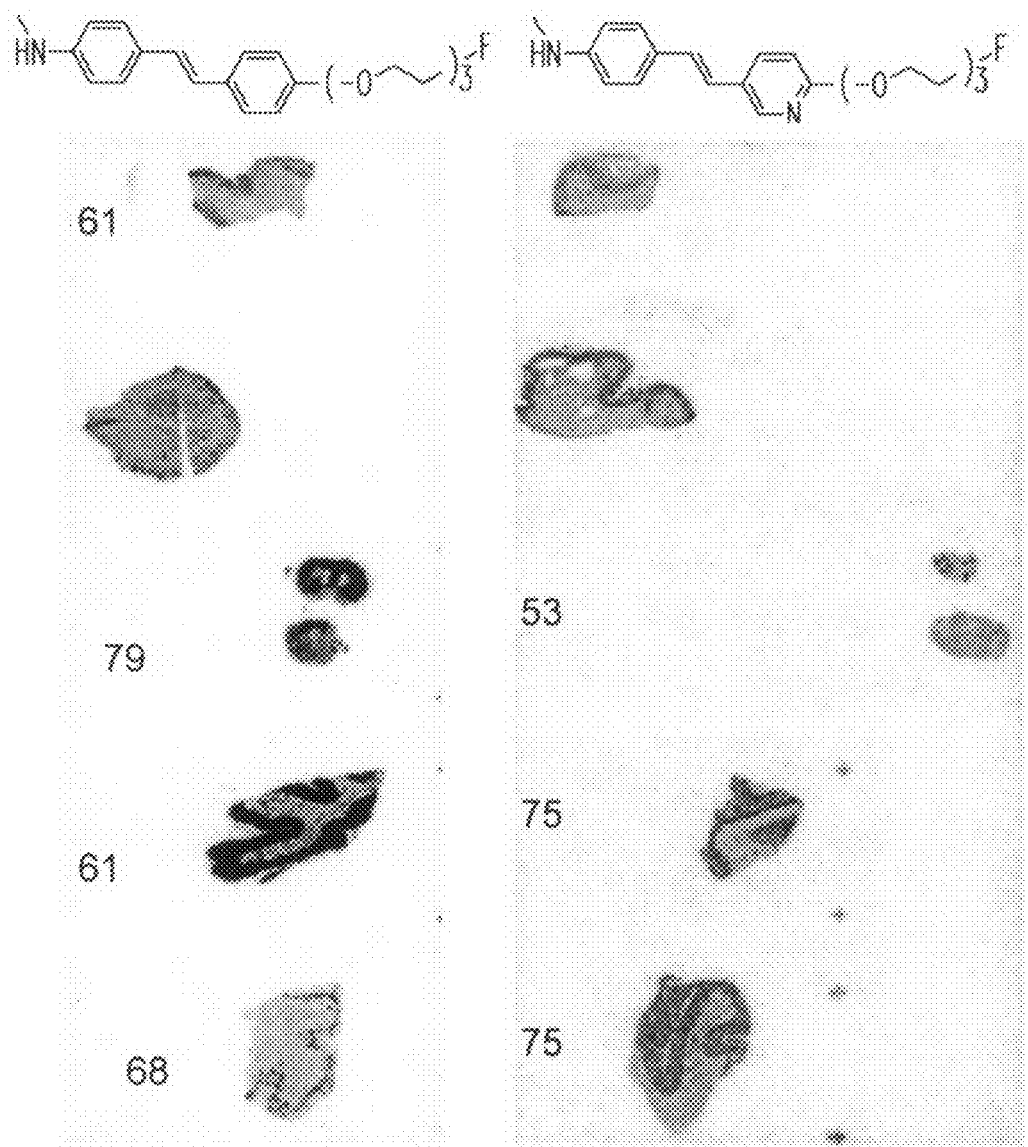
FIG. 3 depicts film autoradiography comparing styrylpyridine 2 in comparison to a stilbene analog.

Delete Figure 3 and replace with the following:

FIG. 3

Figure 4:
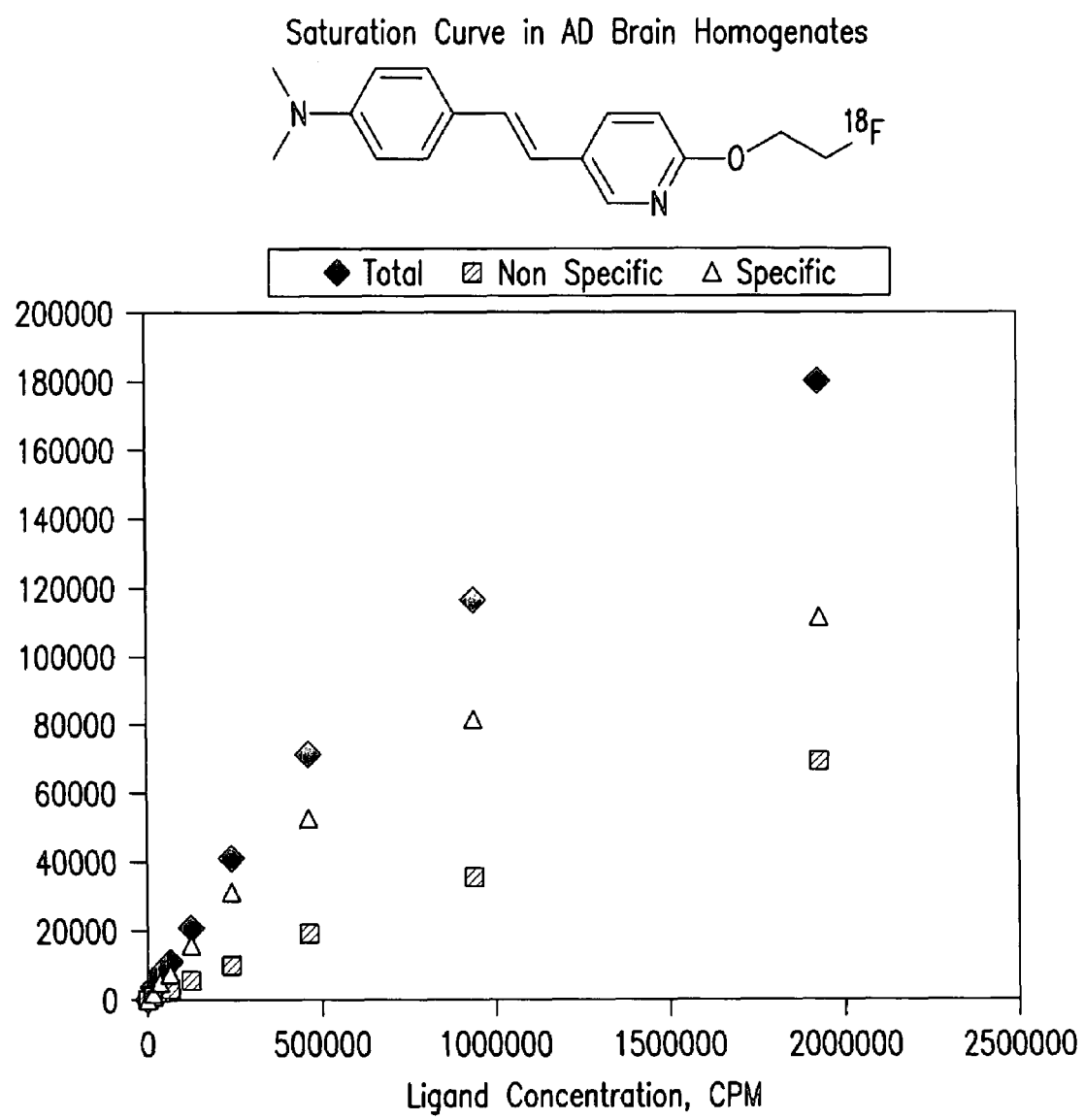
FIG. 4 depicts a saturation curve of styrylpyridine 2 in AD brain homogenates.

Delete Figure 4 and replace with the following:

CERTIFICATE OF CORRECTION (continued)
U.S. Pat. No. 7,687,052 B2

Column 40, lines 38-65, delete Table 1 and replace with the following:

Table 1. Biodistribution in ICR mice after iv injection of [$^{18}$F]2 in 5% EtOH in saline (%dose/g, avg of 3 mice ± SD)

| Organ | 2 min | 30 min | 1 hr | 2 hr |
|---|---|---|---|---|
| Blood | 6.05 ±0.33 | 2.65 ±0.22 | 3.48 ±0.47 | 2.15 ±0.25 |
| Heart | 0.75 ±0.14 | 0.17 ±0.03 | 0.22 ±0.03 | 0.18 ±0.08 |
| Muscle | 7.03 ±1.30 | 8.58 ±0.26 | 10.62 ±2.59 | 5.96 ±0.06 |
| Lung | 1.07 ±0.20 | 0.30 ±0.01 | 0.35 ±0.07 | 0.20 ±0.36 |
| Kidney | 6.38 ±0.95 | 1.68 ±0.11 | 1.96 ±0.21 | 0.96 ±1.58 |
| Spleen | 0.43 ±0.11 | 0.15 ±0.05 | 0.13 ±0.03 | 0.10 ±0.17 |
| Liver | 24.90 ±1.49 | 9.26 ±0.83 | 10.52 ±2.18 | 6.86 ±0.59 |
| Skin | 2.52 ±0.24 | 3.99 ±0.34 | 4.42 ±0.65 | 2.91 ±0.16 |
| Brain | 3.49 ±0.58 | 0.48 ±0.07 | 0.55 ±0.10 | 0.37 ±0.08 |
| Bone | 5.97 ±0.56 | 2.52 ±0.34 | 4.39 ±0.40 | 6.49 ±0.08 |
| Organ | 2 min | 30 min | 1 hr | 2 hr |
| Blood | 3.04 ±0.29 | 1.33 ±0.16 | 1.80 ±0.16 | 1.08 ±0.06 |
| Heart | 6.00 ±1056 | 1.28 ±0.16 | 1.66 ±0.24 | 1.32 ±0.33 |
| Muscle | 0.62 ±0.10 | 0.75 ±0.04 | 0.95 ±0.18 | 0.52 ±0.08 |
| Lung | 5.65 ±0.89 | 1.73 ±0.17 | 1.82 ±0.31 | 0.98 ±0.08 |
| Kidney | 14.19 ±2.34 | 3.77 ±0.36 | 4.29 ±0.52 | 2.19 ±0.36 |
| Spleen | 4.65 ±0.76 | 1.57 ±0.51 | 1.56 ±0.17 | 1.14 ±0.18 |
| Liver | 17.00 ±0.69 | 7.21 ±0.69 | 8.13 ±1.42 | 4.96 ±0.90 |
| Skin | 0.59 ±0.03 | 0.93 ±0.13 | 1.06 ±0.09 | 0.68 ±0.16 |
| Brain | 7.77 ±1.34 | 1.03 ±0.11 | 1.28 ±0.20 | 0.84 ±0.08 |
| Bone | 1.49 ±0.08 | 0.63 ±0.12 | 1.13 ±0.01 | 1.64 ±0.50 |

--                                                                                --.